(12) United States Patent
Takahashi

(10) Patent No.: US 9,668,657 B2
(45) Date of Patent: Jun. 6, 2017

(54) BIOLOGICAL INFORMATION PROCESSING SYSTEM AND METHOD OF CONTROLLING THE SAME

(71) Applicant: Seiko Epson Corporation, Tokyo (JP)

(72) Inventor: Eizo Takahashi, Asahi-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/754,258

(22) Filed: Jun. 29, 2015

(65) Prior Publication Data

US 2016/0005290 A1   Jan. 7, 2016

(30) Foreign Application Priority Data

Jul. 1, 2014   (JP) .................... 2014-135616

(51) Int. Cl.
*G08B 23/00* (2006.01)
*A61B 5/024* (2006.01)
*A61B 5/00* (2006.01)

(52) U.S. Cl.
CPC ............ *A61B 5/024* (2013.01); *A61B 5/4812* (2013.01); *A61B 5/681* (2013.01); *A61B 2505/07* (2013.01)

(58) Field of Classification Search
CPC ...... G04G 21/025; G04G 13/02; A61B 5/024; A61B 5/4812; A61B 5/681; A61B 2505/07
See application file for complete search history.

(56) References Cited

U.S. PATENT DOCUMENTS

| | | | |
|---|---|---|---|
| 6,236,622 B1* | 5/2001 | Blackman | G04B 47/00 362/253 |
| 2008/0306396 A1* | 12/2008 | Ariav | A61B 5/113 600/527 |
| 2013/0163394 A1* | 6/2013 | Loree, IV | G04G 11/00 368/256 |
| 2014/0107520 A1* | 4/2014 | Hang | A61B 5/1036 600/544 |
| 2014/0269223 A1* | 9/2014 | Mokhnatkina | G04G 13/02 368/73 |
| 2015/0026647 A1* | 1/2015 | Park | G06F 3/0488 715/863 |
| 2016/0007931 A1* | 1/2016 | Rubin | A61B 5/02438 600/484 |

FOREIGN PATENT DOCUMENTS

JP   2009-232925 A   10/2009

* cited by examiner

*Primary Examiner* — Erin File
(74) *Attorney, Agent, or Firm* — Kilpatrick Townsend & Stockton LLP

(57) ABSTRACT

A biological information processing system includes a pulse wave information acquisition unit that acquires pulse wave information of a user; and a processing unit that instructs an alarm control unit to perform alarm cancellation when it is determined that the user has transitioned from a sleep state to an awakened state, on the basis of the pulse wave information.

19 Claims, 17 Drawing Sheets

PULSE AC

FREQUENCY ically easily measuring brain waves by reduc-
BIOLOGICAL INFORMATION PROCESSING SYSTEM AND METHOD OF CONTROLLING THE SAME This application claims priority to Japanese Patent Application No. 2014-135616, filed Jul. 1, 2014, the entirety of which is hereby incorporated by reference.

BACKGROUND

1. Technical Field

The present invention relates to a biological information processing system, a method of controlling the same, and the like.

2. Related Art

Hitherto, there has been known a device, such as an alarm clock, which makes a user transition from a sleep state to an awakened state. In addition, notification modes of such a device performing an alarm notification have become diversified, and thus not only a sound such as a bell or a chime but also various sounds such as a natural sound like a birdcall and a human voice are often used. Further, there has been also known a device that performs an alarm notification based on not only a stimulus of a sound but also light or vibration (in a broader sense, a stimulus working on the sense of touch).

In addition, the study of a sleep state has been performed. For example, it has become clear that how to perform transition from a sleep state to an awakened state allows a user to pleasantly get up. Various methods of determining a sleep state are considered. For example, it is possible to determine the depth of sleep, and the like by using brain waves.

In view of such circumstances, a device performing an alarm notification can realize an operation which is more desirable for a user by changing its operation in accordance with a state of the user, instead of operating at the hour which is set in advance.

For example, JP-A-2009-232925 discloses a method of detecting the body motion of a user (sleeper) using a body motion detection sensor and controlling the operation of an alarm apparatus on the basis of a detection result.

In JP-A-2009-232925, the body motion of a user is detected by the body motion detection sensor using infrared light. However, in the body motion detection sensor, as disclosed in JP-A-2009-232925, even though it is possible to discriminate between a state where a user is lying on a bed and a state where a user has gotten up, it is difficult to determine a sleep state and a state where a user is lying down but awake with a high level of accuracy. The body motion sensor detects the motion of a user which can be seen from appearance. Since the user moves very little in a state where the user is resting on a bed while being awake, there is a small difference compared to a sleep state. This is the same as in a case where an acceleration sensor or the like is used as a body motion sensor.

In addition, as described above, it is possible to determine a sleep state and an awakened state with a high level of accuracy by using a sensor (for example, plurality of electrodes) which detects brain waves. However, it is premised that brain waves are measured in a specialized institution such as a medical institution. In addition, a method (apparatus) of relatively easily measuring brain waves by reducing the number of electrodes used has been proposed, but it is not easy to use the method in general homes on a daily basis.

SUMMARY

An advantage of some aspects of the invention is to provide a biological information processing system that determines a sleep state and an awakened state of a user easily and with a high level of accuracy by using pulse wave information and performs a control instruction for an alarm on the basis of a determination result, a method of controlling the biological information processing system, and the like.

An aspect of the invention relates to a biological information processing system including a pulse wave information acquisition unit that acquires pulse wave information of a user; and a processing unit that instructs an alarm control unit to perform alarm cancellation when it is determined that the user has transitioned from a sleep state to an awakened state, on the basis of the pulse wave information.

In the aspect of the invention, it is determined that transition from a sleep state to an awakened state has been performed, on the basis of pulse wave information, and an instruction for alarm cancellation is given on the basis of a determination result. Accordingly, since the pulse wave information is used, it is possible to determine a sleep state and an awakened state relatively easily and with a high level of accuracy and to perform alarm control in consideration of the determination result.

In the aspect of the invention, the processing unit may instruct the alarm control unit to perform alarm cancellation when it is determined that the user has transitioned from the sleep state to the awakened state and that the awakened state has been continued for a predetermined period of time, on the basis of the pulse wave information.

With this configuration, since an instruction for alarm cancellation is given when an awakened state is continued for a certain extent, it is possible to perform appropriate alarm control.

In the aspect of the invention, the processing unit may instruct the alarm control unit to set an alarm when it is determined that the user has transitioned from the awakened state to the sleep state, on the basis of the pulse wave information.

With this configuration, since an instruction for setting an alarm is given when it is determined that transition to a sleep state has been performed, it is possible to perform appropriate alarm control.

In the aspect of the invention, the processing unit may instruct the alarm control unit to set an alarm when it is determined that the user has transitioned from the awakened state to the sleep state and that the sleep state has been continued for a predetermined period of time, on the basis of the pulse wave information.

With this configuration, since an instruction for setting an alarm is given when a sleep state is continued for a certain extent, it is possible to appropriately perform alarm control.

In the aspect of the invention, when the processing unit determines that the user has transitioned from the sleep state to the awakened state and that the awakened state has been continued for a predetermined period of time, on the basis of the pulse wave information, and instructs the alarm control unit to perform alarm cancellation, the processing unit may not give an instruction for setting of an alarm even when it is determined that the user has transitioned from the awakened state to the sleep state after the alarm cancellation is performed, on the basis of the pulse wave information.

With this configuration, since an instruction for setting an alarm can be skipped when there is an instruction for alarm cancellation, it is possible to perform appropriate alarm control.

In the aspect of the invention, when the processing unit determines that the user has transitioned from the sleep state to the awakened state and that the awakened state has been continued for a predetermined period of time, on the basis of the pulse wave information, and instructs the alarm control unit to perform alarm cancellation, the processing unit may give an instruction for setting of an alarm even when it is determined that the user has transitioned from the awakened state to the sleep state after the alarm cancellation is performed, on the basis of the pulse wave information.

With this configuration, since an instruction for setting an alarm can be given again even when there is an instruction for alarm cancellation, it is possible to perform appropriate alarm control.

In the aspect of the invention, the processing unit may determine an autonomic nerve activity state on the basis of the pulse wave information, and may determine the sleep state and the awakened state on the basis of the autonomic nerve activity state.

With this configuration, it is possible to determine the sleep state and the awakened state on the basis of the autonomic nerve activity state.

In the aspect of the invention, the processing unit may determine an autonomic nerve activity state and a biological activity state on the basis of the pulse wave information, and may determine the sleep state and the awakened state on the basis of the autonomic nerve activity state and the biological activity state.

With this configuration, it is possible to determine the sleep state and the awakened state on the basis of the autonomic nerve activity state and the biological activity state.

In the aspect of the invention, the biological information processing system may further include a body motion information acquisition unit that acquires body motion information of the user. The processing unit may determine the sleep state and the awakened state on the basis of the pulse wave information and the body motion information.

With this configuration, it is possible to determine the sleep state and the awakened state on the basis of the pulse wave information and the body motion information.

In the aspect of the invention, the biological information processing system may further include the alarm control unit.

With this configuration, it is possible to perform alarm control itself in the biological information processing system.

Another aspect of the invention relates to a biological information processing system that acquires pulse wave information of a user and performs alarm cancellation when it is determined that the user has transitioned from a sleep state to an awakened state on the basis of the pulse wave information.

In the aspect of the invention, when it is determined that transition from a sleep state to an awakened state has been performed, on the basis of pulse wave information, an alarm is cancelled on the basis of a determination result. Accordingly, since the pulse wave information is used, it is possible to determine a sleep state and an awakened state relatively easily and with a high level of accuracy and to perform alarm control in consideration of the determination result.

In the aspect of the invention, when it is determined that the user has transitioned from the sleep state to the awakened state and that the awakened state has been continued for a predetermined period of time, on the basis of the pulse wave information, an alarm may be cancelled.

With this configuration, since alarm cancellation is performed when an awakened state is continued for a certain extent, it is possible to appropriately perform alarm control.

In the aspect of the invention, when it is determined that the user has transitioned from the awakened state to the sleep state on the basis of the pulse wave information, an alarm may be set.

With this configuration, since an alarm is set when it is determined that transition to a sleep state has been performed, it is possible to appropriately perform alarm control.

In the aspect of the invention, when it is determined that the user has transitioned from the awakened state to the sleep state and that the sleep state has been continued for a predetermined period of time, on the basis of the pulse wave information, an alarm may be set.

With this configuration, since an alarm is set when a sleep state is continued for a certain extent, it is possible to appropriately perform alarm control.

In the aspect of the invention, when it is determined that the user has transitioned from the sleep state to the awakened state and that the awakened state has been continued for a predetermined period of time, on the basis of the pulse wave information, and alarm cancellation is performed, an alarm may not be set even when it is determined that the user has transitioned from the awakened state to the sleep state after the alarm cancellation is performed, on the basis of the pulse wave information.

With this configuration, since the setting of an alarm can be skipped when alarm cancellation is performed, it is possible to appropriately perform alarm control.

In the aspect of the invention, when it is determined that the user has transitioned from the sleep state to the awakened state and that the awakened state has been continued for a predetermined period of time, on the basis of the pulse wave information, and alarm cancellation is performed and when it is determined that the user has transitioned from the awakened state to the sleep state after the alarm cancellation is performed, on the basis of the pulse wave information, an alarm may be set.

With this configuration, since an instruction for setting an alarm can be given when alarm cancellation is performed, it is possible to appropriately perform alarm control.

In the aspect of the invention, an autonomic nerve activity state may be determined on the basis of the pulse wave information, and the sleep state and the awakened state may be determined on the basis of the autonomic nerve activity state.

With this configuration, it is possible to determine the sleep state and the awakened state on the basis of the autonomic nerve activity state.

In the aspect of the invention, an autonomic nerve activity state and a biological activity state may be determined on the basis of the pulse wave information, and the sleep state and the awakened state may be determined on the basis of the autonomic nerve activity state and the biological activity state.

With this configuration, it is possible to determine the sleep state and the awakened state on the basis of the autonomic nerve activity state and the biological activity state.

In the aspect of the invention, body motion information of the user may be acquired, and the sleep state and the awakened state may be determined on the basis of the pulse wave information and the body motion information.

With this configuration, it is possible to determine the sleep state and the awakened state on the basis of the pulse wave information and the body motion information.

Still another aspect of the invention relates to a method of controlling a biological information processing system, the method including performing a process of acquiring pulse wave information of a user; and performing alarm cancellation when it is determined that the user has transitioned from a sleep state to an awakened state, on the basis of the pulse wave information.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
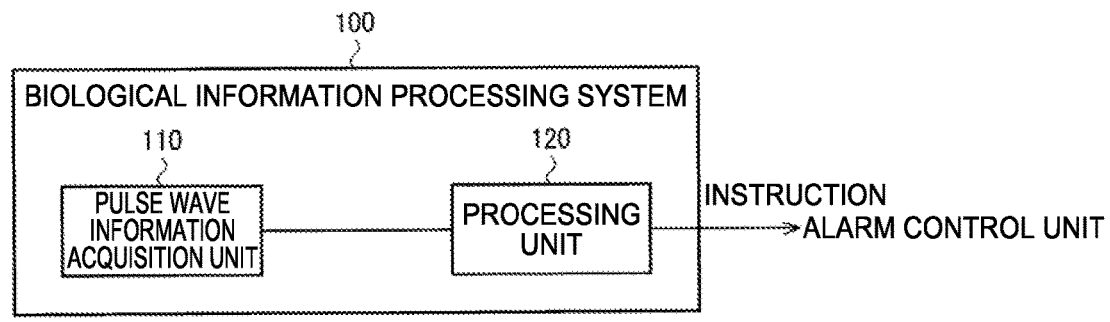
FIG. 1 illustrates a configuration example of a biological information processing system according to the present embodiment.

Hereinafter, the present embodiment will be described. Meanwhile, the present embodiment to be described below is not unduly limited to the disclosure of the invention described in the aspects. In addition, all the configurations described below are not necessarily essential components of the invention.

1. Method According to the Present Embodiment

First, a method according to the present embodiment will be described. As described above, modes of an alarm notification using a device (for example, an alarm clock) which has a function of an alarm clock have diversified, and thus light, vibration, and the like have been used, in addition to a sound such as a bell or a chime and a human voice which have been used hitherto.

In addition, there has been known a device that has a more complicated and advanced function with respect to not only a mode of an alarm notification but also the setting and cancellation (ON and OFF) of an alarm. For example, JP-A-2009-232925 mentioned above discloses that an alarm is controlled on the basis of a detection result of the body motion of a user.

In this case, the problem is under what conditions the mode of an alarm notification, alarm setting, and alarm cancellation are controlled. For example, when the notification mode, the alarm setting, and the alarm cancellation are controlled as set in advance (statically), it is difficult to realize a system which is easy for a user to use. This is because a situation may occur where a user desires to perform an alarm notification at a usual time, and on the contrary, a situation may occur where there is preferably no alarm notification at usual times, whereby it is not possible to cope with variations in the situations in the above-mentioned static setting. In addition, it has become clear through recent research for sleep that an alarm notification is preferably performed when a user is in some sleep state or what mode of notification is preferably selected as an alarm notification. However, it is still difficult to perform alarm control based on the preferable modes of control based on the static setting.

On the other hand, it is considered that information regarding a state of a user, particularly, a sleep state and an awakened state is acquired by some units and alarm control is performed using the information. In this manner, it is possible to realize dynamic alarm control according to the state of the user.

Here, a method of determining a sleep state of a user to thereby perform alarm control is disclosed in the related art such as JP-A-2009-232925. In JP-A-2009-232925, determination is performed using a body motion sensor. However, the body motion sensor detects the motion of the user motion which can be seen from appearance. Since there is extremely little motion in a state where a user is resting on a bed while being awake, a difference from a sleep state is small. For this reason, in the body motion sensor, the accuracy of determination of whether a user is in a sleep state or an awakened state is low. Further, when a person is in a sleep state, the sleep depth thereof changes with time as described later with reference to FIG. 9, and can be considered to be divided into some stages. However, it is extremely difficult to discriminate between such detailed stages.

In addition, a method using brain waves for the determination of a sleep state is well known. Specifically, a plurality (for example, several tens) of electrodes for detecting brain waves are mounted to a user's head, and a sleep state is determined using the fact that brain waves having different characteristics depending on the state (depth) of sleep are detected. In a case where brain waves are used, it is possible to determine a sleep state with a high level of accuracy.

However, it is premised that brain waves are measured in a specialized institution such as a medical institution. In addition, there has been proposed a method (apparatus) of relatively easily measuring brain waves by reducing the number of electrodes used and by integrally configuring a plurality of electrodes in one apparatus, but it is not easy to use the method in general homes on a daily basis.

Consequently, the applicant proposes a method of acquiring pulse wave information of a user by a pulse wave sensor and performing alarm control using the pulse wave information. Specifically, as illustrated in FIG. 1, a biological information processing system 100 according to the present embodiment includes a pulse wave information acquisition unit 110 that acquires pulse wave information of a user and a processing unit 120 that instructs an alarm control unit (alarm control unit 130 in an example of FIG. 2A to be described later) to perform alarm cancellation when it is determined that a user transitions from a sleep state to an awakened state on the basis of the pulse wave information.

In this manner, when it is determined that the user transitions from a sleep state to an awakened state, it is possible to cancel (OFF) an alarm. As a specific situation, a case where the user transitions to an awakened state before an alarm hour which is set in advance is considered. In this case, since the user is already in an awakened state, there is no advantage of further performing an alarm notification. In contrast, there is a concern of the user having an unpleasant feeling due to an unnecessary alarm notification (for example, by making a loud sound) in spite of already being in an awakened state. In this respect, the cancellation of an alarm in the case of transition to an awakened state can allow the execution of an unnecessary alarm notification to be suppressed.

Figure 5:
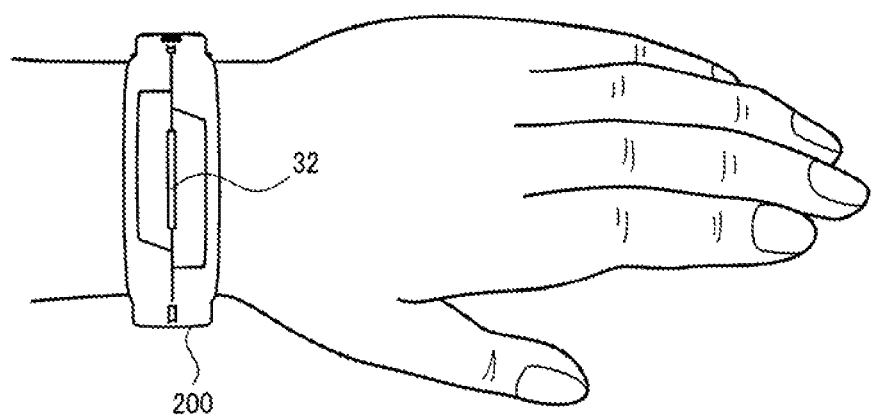
FIG. 5 is an example in which the biological information processing system (wearable apparatus) is worn by a user.

In addition, it is possible to realize such alarm control using pulse wave information. A pulse wave sensor for acquiring pulse wave information can be realized by, for example, a photoelectric sensor. The photoelectric sensor may be preferably formed by combining a light emitting unit (for example, an LED) and a light receiving unit (for example, a PD), and thus can be easily realized in a hardware manner. In addition, it is possible to reduce the size of a sensor unit or the entire apparatus even when a plurality of sets each of which is constituted by an LED and a PD are provided in consideration of an improvement in accuracy. In addition, it is not necessary to mount a sensor at a plurality of different locations like for brain waves, and there is no problem even when only a wrist is set as a mounting location, for example, as illustrated in FIG. 5 to be described later. In other words, it is easy to reduce the cost, size, and weight of an apparatus for detecting pulse waves, and troublesomeness at the time of mounting the apparatus is not a problem, and thus there is an advantage as compared with the detection of brain waves. In addition, since it is possible to detect internal information of a user (specifically, changes in blood flow of a user, and the like) unlike a body motion sensor, it is possible to determine a sleep state with high accuracy as compared to a case where body motion is used.

Meanwhile, the biological information processing system 100 according to the present embodiment is not limited to a system that gives an instruction for alarm cancellation on the basis of a determination result using pulse wave information. For example, the biological information processing system 100 may be a system that acquires pulse wave information of a user and cancels an alarm when it is determined that a user transitions from a sleep state to an awakened state on the basis of the pulse wave information. In other words, control regarding an alarm may be preferably performed using a determination result based on the pulse wave information, and the biological information processing system 100 of the present embodiment is not limited to some instructions in the process and the associations with the execution of the instructions.

In addition, as illustrated in FIG. 1, when attention is paid to a notification mode of an alarm, the biological information processing system 100 according to the present embodiment includes the pulse wave information acquisition unit 110 that acquires pulse wave information of a user and the processing unit 120 that determines a sleep state of a user on the basis of the pulse wave information and instructs an alarm control unit to perform an alarm notification based on a notification mode according to a sleep state.

Here, specifically, the determination of a sleep state may be determination of the depth of sleep. For example, it is determined whether the sleep is in a REM sleep state or a non-REM sleep state. In addition, non-REM sleep is known to have four stages from stage 1 to stage 4, and determination having a high accuracy may be performed even in consideration of the stages in determining a sleep state.

In this manner, since it is possible to set an appropriate notification mode of an alarm in accordance with a sleep state, it is possible to perform an alarm notification for promoting a user to spontaneously wake up. Detailed control of a notification mode will be described later.

In addition, the invention is not limited to an embodiment in which an instruction for alarm notification and the execution of the instruction are performed. For example, the biological information processing system 100 may determine a sleep state of a user on the basis of pulse wave information of the user and may perform an alarm notification based on a notification mode according to the sleep state.

Hereinafter, a configuration example of the biological information processing system 100 according to the present embodiment will be described, and then a specific alarm control method using a determination result such as a sleep state will be described. Specifically, control for cancelling an alarm, control for setting (ON) an alarm, and control for determining a notification mode of an alarm will be described. Finally, the determination of a sleep state using pulse wave information will be described.

2. Configuration Example of System

As illustrated in FIG. 1, the biological information processing system 100 according to the present embodiment includes the pulse wave information acquisition unit 110 and the processing unit 120. The pulse wave information acquisition unit 110 acquires sensor information from a pulse wave sensor. Here, the pulse wave sensor is a sensor for detecting a pulse wave signal. For example, a photoelectric sensor including a light emitting unit and a light receiving unit is considered. It is known that a pulse wave sensor such as a photoelectric sensor or other types of sensors (for example, an ultrasonic sensor) can be realized by various sensors, and these sensors can be widely applied to the pulse wave sensor of the present embodiment.

The processing unit 120 performs determination regarding a sleep state on the basis of the pulse wave information acquired by the pulse wave information acquisition unit 110 and gives an instruction to an alarm control unit on the basis of a determination result. The functions of the processing unit 120 can be realized by various processors (CPU and the like), hardware such as an ASIC (gate array and the like), a program, and the like. However, the biological information processing system 100 is not limited to the configuration of FIG. 1 and various modifications such as an omission of some components or addition of other components can be made. In addition, the fact that modifications can be made is the same as in FIGS. 2A to 2C, FIG. 7, FIG. 8, and the like.

Figure 2A:
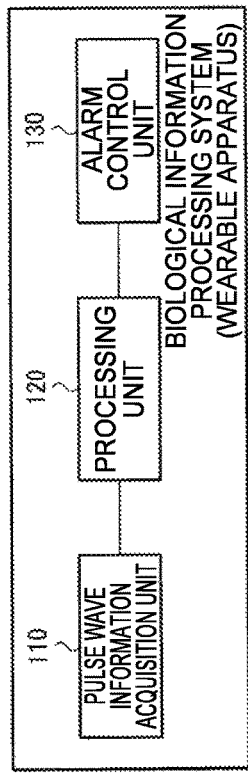
FIGS. 2A to 2C illustrate other configuration examples of the biological information processing system according to the present embodiment.

For example, the biological information processing system 100 according to the present embodiment may further include an alarm control unit that controls an alarm. Specifically, when the biological information processing system 100 is realized by a single wearable apparatus 200 (band-type apparatus worn on a wrist in an example of FIG. 5 to be described later), the biological information processing system 100 includes the pulse wave information acquisition unit 110, the processing unit 120, and an alarm control unit 130 as illustrated in FIG. 2A. Although not shown in FIG. 2A, the biological information processing system 100 (wearable apparatus 200) may include a pulse wave sensor and a notification unit.

In this manner, it is possible to perform alarm control (and an alarm notification based on the control) within the biological information processing system 100. Accordingly, for example, it is possible to perform both the determination of a sleep state and alarm control with a simple configuration of the single wearable apparatus 200 illustrated in FIG. 2A.

Figure 3A:
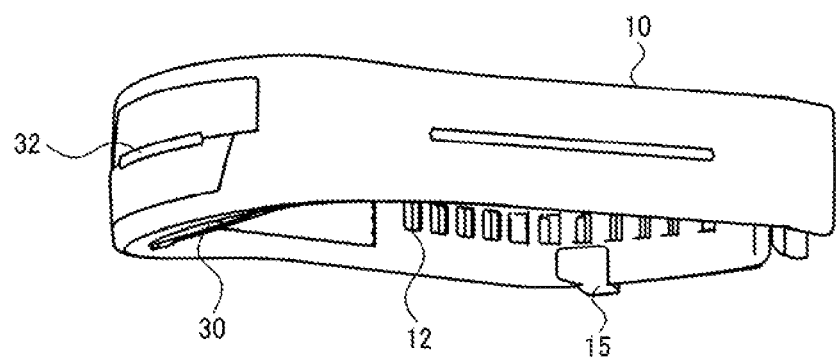
FIGS. 3A and 3B are diagrams illustrating an exterior of the biological information processing system (wearable apparatus) according to the present embodiment.
Figure 3B:
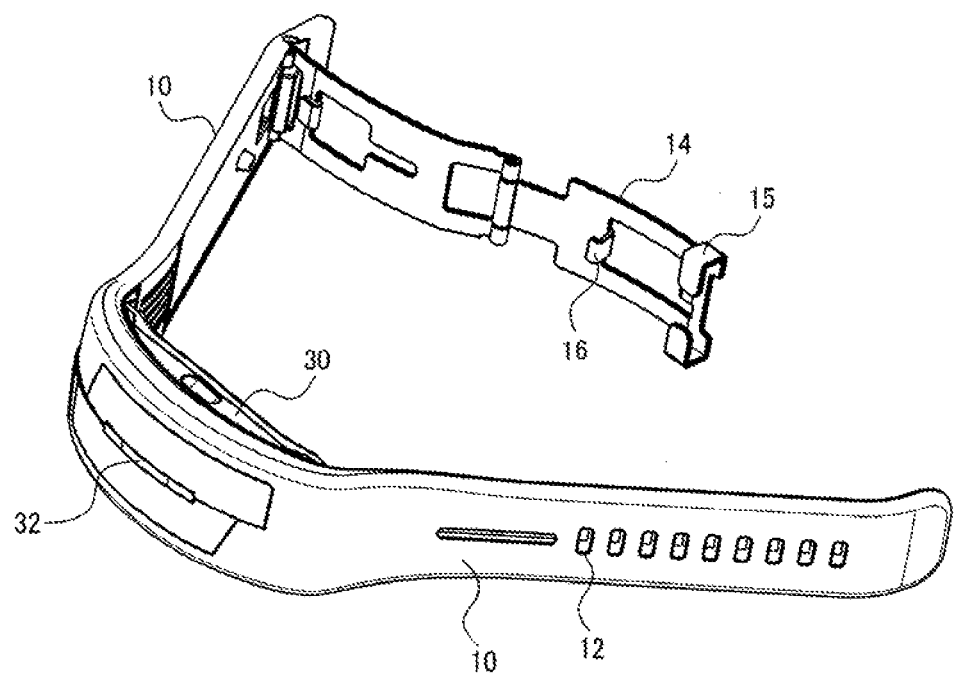
Figure 4:
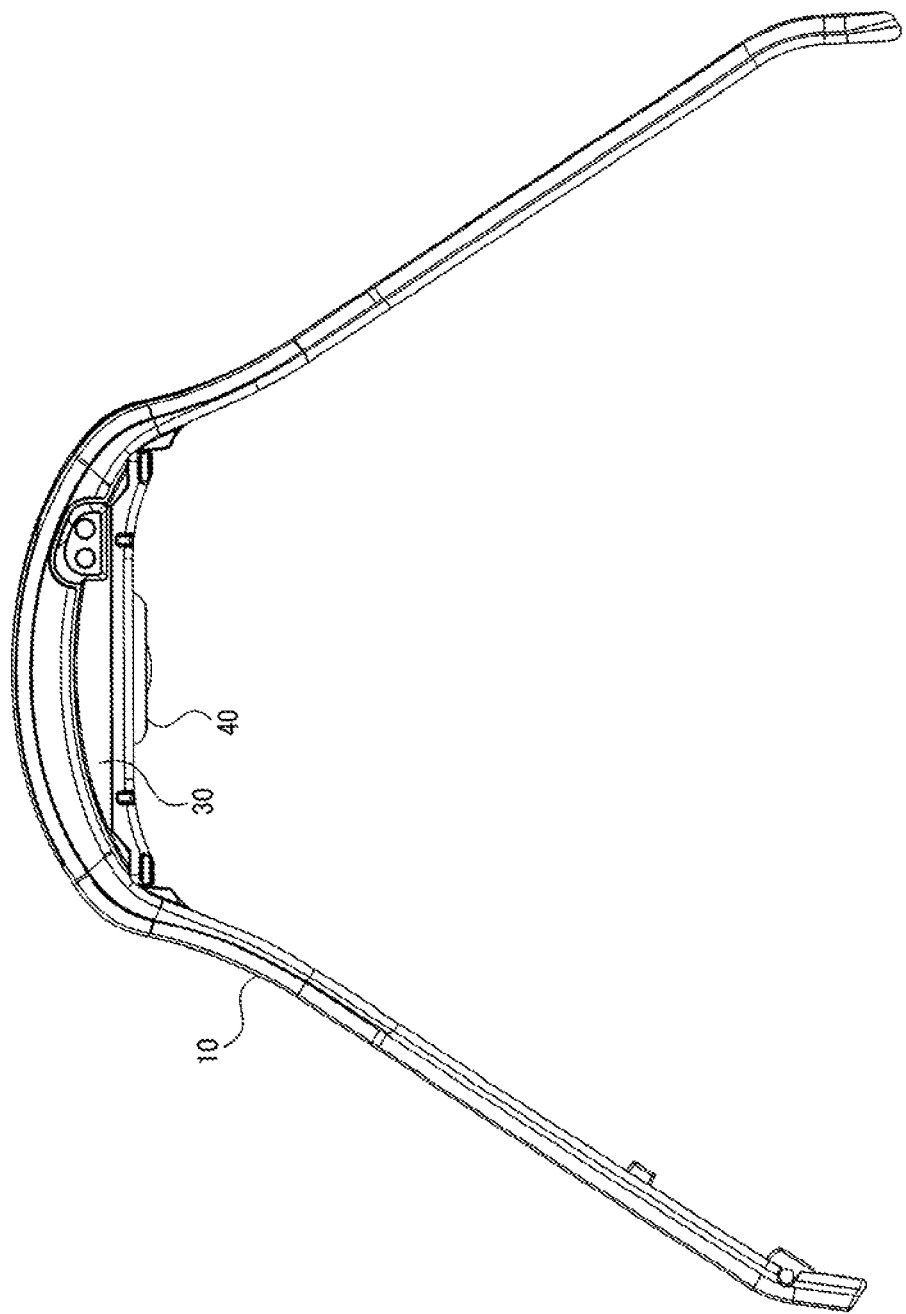
FIG. 4 is a diagram illustrating an exterior of the biological information processing system (wearable apparatus) according to the present embodiment.

FIGS. 3A and 3B and FIG. 4 illustrate an example of a diagram illustrating the exterior of the biological information processing system 100 (wearable apparatus 200) according to the present embodiment. The wearable apparatus 200 of the present embodiment includes a band portion 10, a case portion 30, and a sensor unit 40. The case portion 30 is mounted to the band portion 10. The sensor unit 40 is provided in the case portion 30.

The band portion 10 is used to wind the wearable apparatus 200 around a user's wrist and have the apparatus worn thereon. The band portion 10 includes a band hole 12 and a buckle portion 14. The buckle portion 14 includes a band insertion portion 15 and a protrusion portion 16. A user inserts one end side of the band portion 10 into the band insertion portion 15 of the buckle portion 14 and inserts the protrusion portion 16 of the buckle portion 14 into the band hole 12 of the band portion 10 to thereby mount the wearable apparatus 200 on the wrist.

The case portion 30 is equivalent to a main body of the wearable apparatus 200. Various components of the wearable apparatus 200, such as the sensor unit 40 and the processing unit 120, are provided within the case portion 30. That is, the case portion 30 is a housing that accommodates these components.

A light emitting window portion 32 is provided in the case portion 30. The light emitting window portion 32 is formed of a translucent member. The case portion 30 is provided with a light emitting unit as an interface mounted on a flexible substrate, and light from the light emitting unit is emitted to the outside of the case portion 30 through the light emitting window portion 32.

The wearable apparatus 200 is worn on a user's wrist as illustrated in FIG. 5, and the measurement of pulse wave information (in a broader sense, biological information) is performed in the worn state.

Figure 2B:
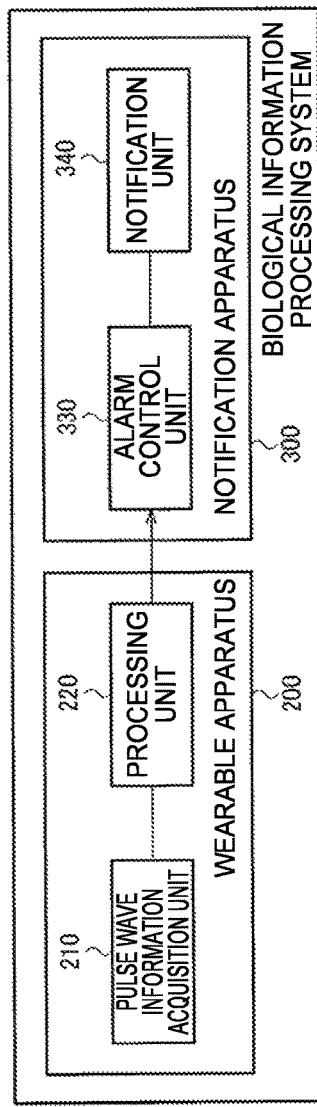

In addition, the biological information processing system 100 of the present embodiment is not limited to a system which is constituted by a single apparatus. For example, as illustrated in FIG. 2B, the biological information processing system 100 may be constituted by an apparatus for determining a sleep state (here, the wearable apparatus 200) and an apparatus for performing an alarm notification (here, a notification apparatus 300). In this case, as illustrated in FIG. 2B, the wearable apparatus 200 includes a pulse wave information acquisition unit 210 and a processing unit 220, and the notification apparatus 300 includes an alarm control unit 330 and a notification unit 340.

Figure 6:
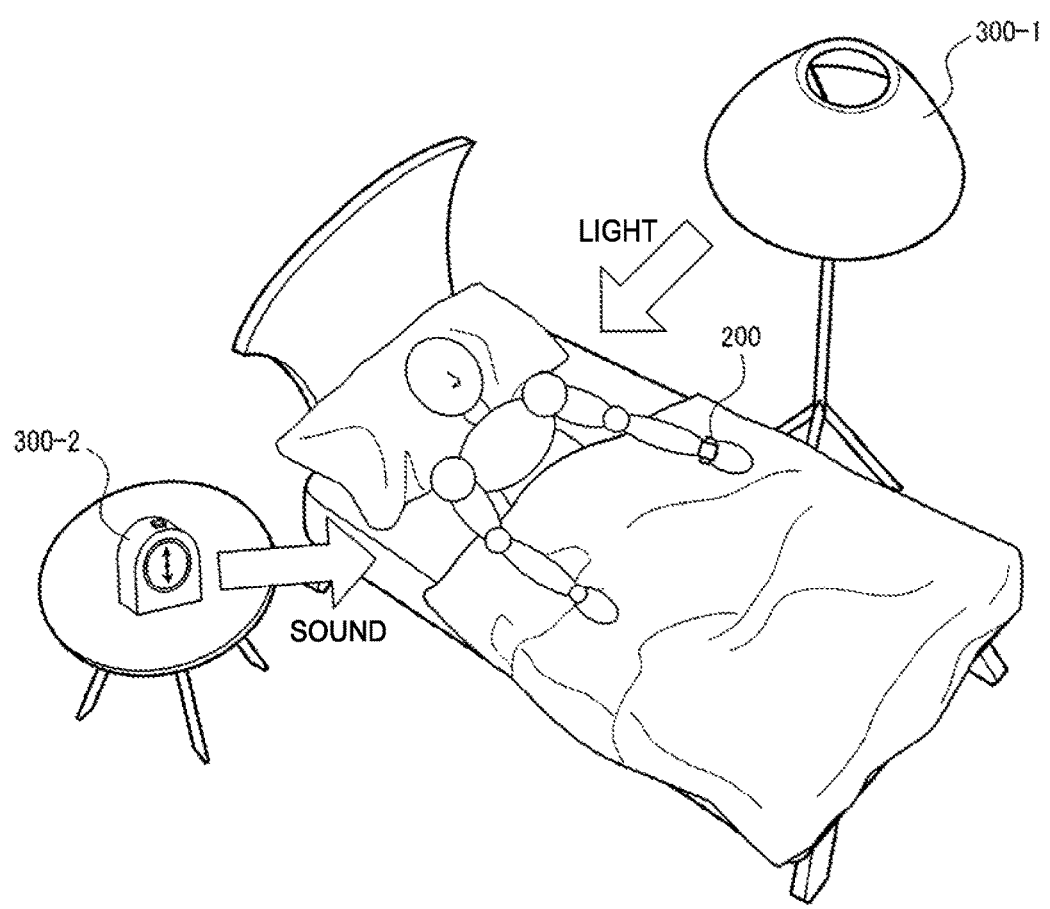
FIG. 6 is an example in which the biological information processing system according to the present embodiment is realized.

In this manner, it is possible to realize the biological information processing system 100 according to the present embodiment by cooperation between a plurality of apparatuses. An example is illustrated in FIG. 6. In FIG. 6, a user wears the band-type wearable apparatus 200 on his or her wrist as illustrated in FIG. 5, and the acquisition of pulse wave information and the determination of a sleep state are performed using a pulse wave sensor included in the wearable apparatus 200. In addition, in FIG. 6, an illumination apparatus 300-1 and an alarm clock 300-2 are disposed as the notification apparatus 300. The illumination apparatus 300-1 performs an alarm notification based on light emission and the control of the alarm notification, and the alarm clock 300-2 performs an alarm notification based on a sound and the control of the alarm notification. Since the wearable apparatus 200 needs to transmit an instruction for alarm control based on a determination result of a sleep state to the notification apparatus 300, the wearable apparatus 200 and the notification apparatus 300 are connected to each other by some communication units (for example, short-range radio communication).

As described above, it is not essential for the biological information processing system 100 according to the present embodiment to include an alarm control unit. In other words, in the system configuration illustrated in FIG. 2B and FIG. 6, only the portion of the wearable apparatus 200 may be used as the biological information processing system 100 according to the present embodiment.

Figure 2C:
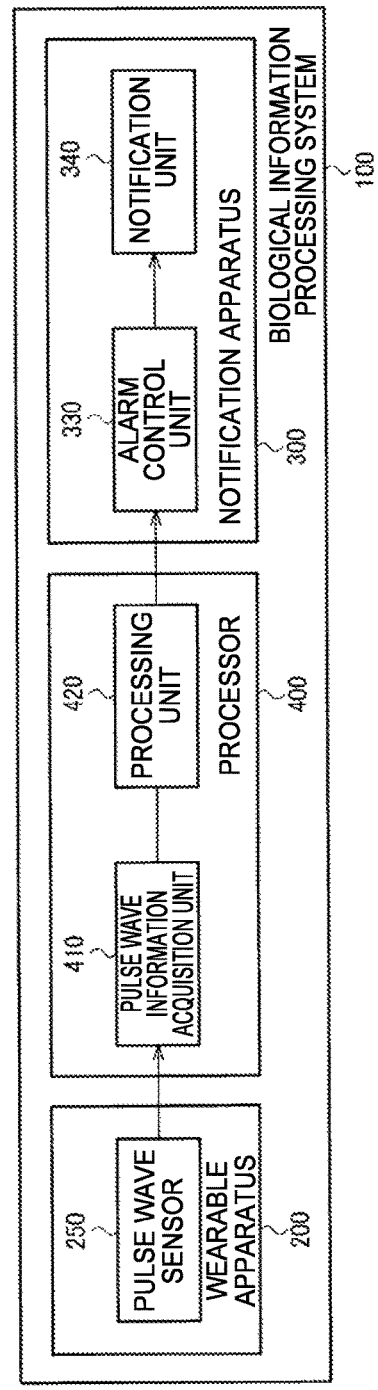

In addition, the biological information processing system 100 of the present embodiment may be constituted by three or more apparatuses. For example, as illustrated in FIG. 2C, the biological information processing system 100 may include the wearable apparatus 200, a processor 400, and the notification apparatus 300. In the example of FIG. 2C, it is assumed that the wearable apparatus 200 includes a pulse wave sensor 250, the processor 400 includes a pulse wave information acquisition unit 410 and a processing unit 420, and the notification apparatus 300 includes an alarm control unit 330 and a notification unit 340.

Here, the processor 400 may be a portable terminal device such as, for example, a smartphone. In this case, the wearable apparatus 200 transmits sensor information of the pulse wave sensor 250 to the processor 400, and a process based on the sensor information is performed by the processor 400. As illustrated in FIG. 5, since the wearable apparatus 200 worn by a user is required to be a small size and light weight, restriction on the processing performance of a battery or a processing unit (the processing unit 120 in the case of FIG. 2A) or the storage capacity of data is great. On the other hand, since the processor 400 has a relatively small restriction on resources, the processor can perform a process of determining a sleep state at a high speed and store more pieces of data (pulse wave information, or a determination result of a sleep state). Further, connection between the wearable apparatus 200 and the processor 400 and connection between the processor 400 and the notification apparatus 300 may be performed using a network such as the Internet. In this case, a server system may be used as the processor 400, and thus the restriction on resources becomes more lax.

As described above, since the biological information processing system 100 may preferably include a pulse wave information acquisition unit and a processing unit, only the portion of the processor 400 may be used as the biological information processing system 100 according to the present embodiment in the system configuration illustrated in FIG. 2C.

Figure 7:
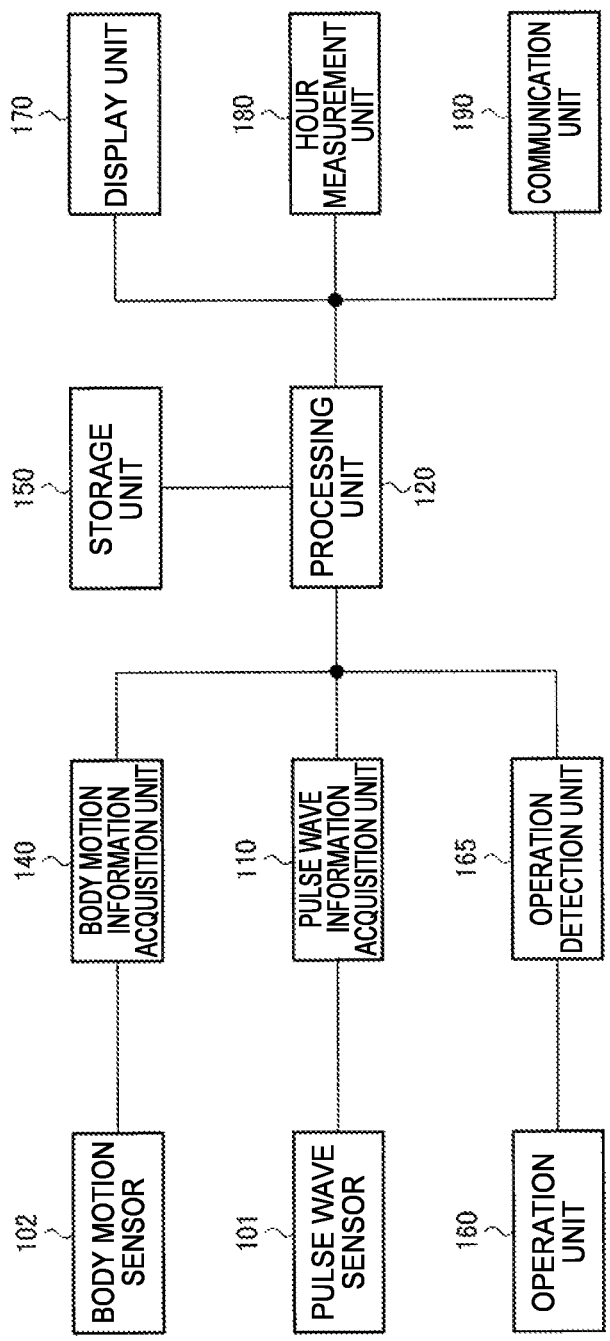
FIG. 7 is a detailed configuration example of the biological information processing system according to the present embodiment.

Next, a specific configuration example of the biological information processing system 100 according to the present embodiment will be described with reference to FIGS. 7 and 8. FIG. 7 is a diagram illustrating functional blocks, which are particularly used to determine a sleep state, in the biological information processing system 100. As illustrated in FIG. 7, the biological information processing system 100 includes a pulse wave sensor 101, a body motion sensor 102, a pulse wave information acquisition unit 110, a processing unit 120, a body motion information acquisition unit 140, a storage unit 150, an operation unit 160, an operation detection unit 165, a display unit 170, an hour measurement unit 180, and a communication unit 190.

The body motion sensor 102 is a sensor that detects the body motion of a user, and it is possible to use various sensors such as an acceleration sensor or a gyro sensor. The body motion information acquisition unit 140 acquires body motion information indicating the body motion of a user on the basis of sensor information from the body motion sensor 102.

The storage unit 150 serves as a work area of the processing unit 120 or the like, and the function thereof can be realized by a memory such as a RAM and a hard disk drive (HDD). The storage unit 150 may store pulse wave information, a determination result of a sleep state, and the like. The operation unit 160 receives a user's operation. Specifically, the operation unit may be realized by a physical button or a lever, or a touch panel or the like may be used. In addition, vibration generated by a user tapping an apparatus may be used as an interface. In this case, the body motion sensor 102 may be used as the operation unit 160. The operation detection unit 165 detects a user's operation on the basis of a signal from the operation unit 160.

The display unit 170 is used to display various types of display screens, and can be realized by, for example, a liquid crystal display or an organic EL display. Meanwhile, in the biological information processing system 100, the display unit 170 may be omitted. In this case, an instruction for information regarding a user may be performed using another method. For example, the biological information processing system 100 including a light emitting unit may present information by the light emission of the light emitting unit, or the biological information processing system including a vibration unit may present information by the vibration of the vibration unit.

The hour measurement unit 180 measures time by the hour. The communication unit 190 communicates with other apparatuses through various networks or the like.

Figure 8:
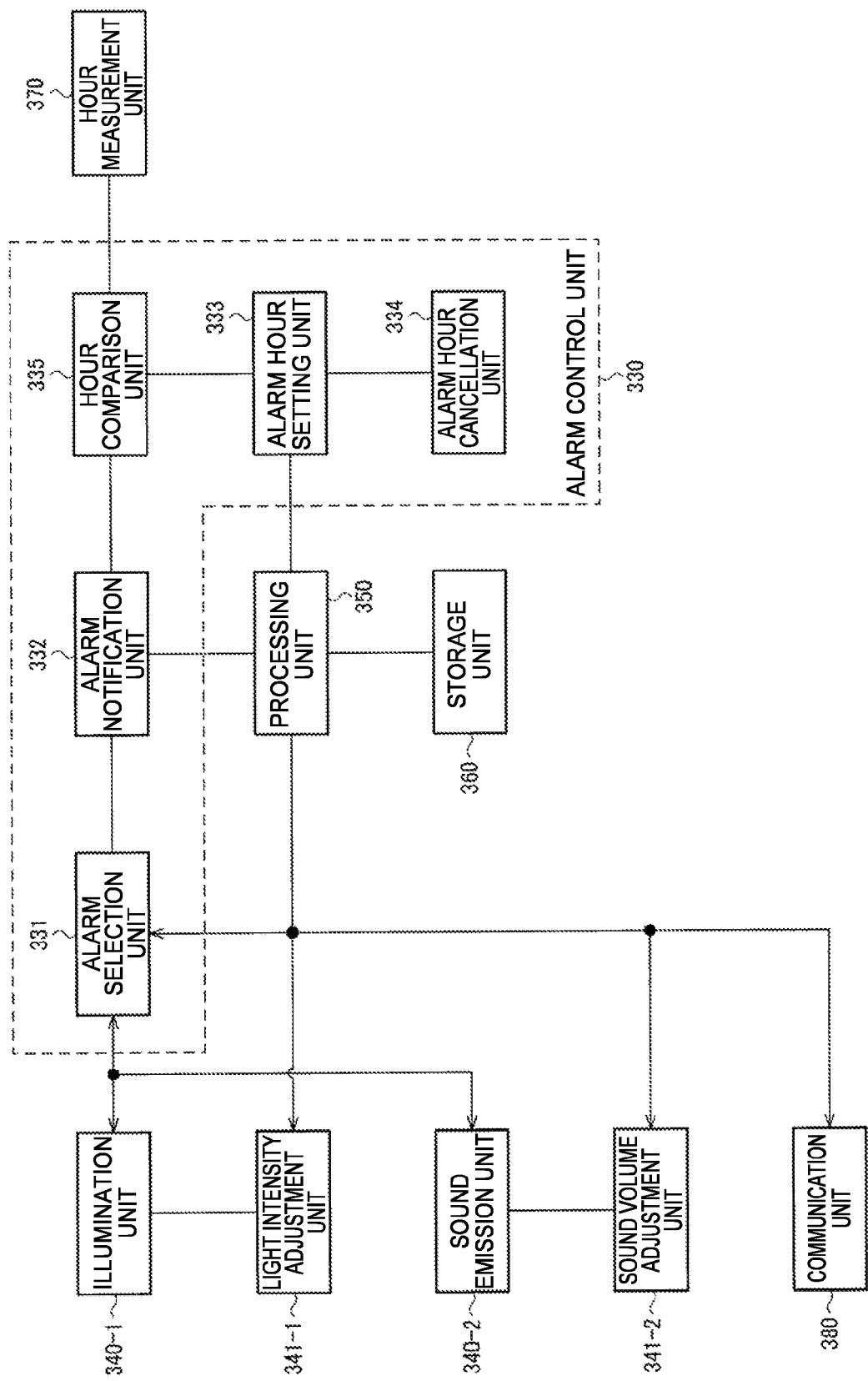
FIG. 8 is another detailed configuration example of the biological information processing system according to the present embodiment.

FIG. 8 is a diagram illustrating functional blocks which are used to perform an alarm notification. Here, similar to FIG. 2B, a configuration example of the notification apparatus 300 is described. However, as described above, it is optional whether or not the notification apparatus 300 is included in the biological information processing system 100. In addition, similarly to FIG. 2A, the functional blocks illustrated in FIG. 8 may be provided within a device including the functional blocks illustrated in FIG. 7.

As illustrated in FIG. 8, the notification apparatus 300 includes an alarm control unit 330, an illumination unit 340-1, a light intensity adjustment unit 341-1, a sound emission unit 340-2, a sound volume adjustment unit 341-2, a processing unit 350, a storage unit 360, an hour measurement unit 370, and a communication unit 380.

The alarm control unit 330 includes an alarm selection unit 331, an alarm notification unit 332, an alarm hour setting unit 333, an alarm hour cancellation unit 334, and an hour comparison unit 335. When the notification unit 340 can select a plurality of notification modes, the alarm selection unit 331 selects in which mode a notification is performed. The alarm notification unit 332 causes the notification unit 340 to perform a notification based on the selected notification mode. The alarm hour setting unit 333 sets the hour at which an alarm notification is performed (performs control for setting an alarm at the hour to be in an ON state). The alarm hour cancellation unit 334 cancels the hour at which an alarm notification is performed (performs control for setting an alarm at the hour to be in an OFF state). The hour comparison unit 335 compares the hour which is set by the alarm hour setting unit 333 with the current hour which is acquired from the hour measurement unit 370.

The illumination unit 340-1, which is an example of the notification unit 340, performs irradiation with illumination light on the basis of the light intensity which is adjusted by the light intensity adjustment unit 341-1. The sound emission unit 340-2, which is an example of the notification unit 340, generates a sound (a natural sound, a voice, a bell, or the like) on the basis of the sound volume which is adjusted by the sound volume adjustment unit 341-2. Meanwhile, FIG. 8 illustrates an example in which one notification apparatus 300 performs two alarm notifications based on light and a sound, but the plurality of notification apparatuses 300 may be provided as illustrated in FIG. 6.

Hereinafter, a pulse wave information acquisition unit is denoted by reference numeral 110, and a processing unit is denoted by reference numeral 120. However, it is possible to consider that the units are replaced with the blocks, such as the pulse wave information acquisition unit 210 and the processing unit 220 illustrated in FIG. 2B and the pulse wave information acquisition unit 410 and the processing unit 420 illustrated in FIG. 2C, which have been described by attaching other reference numerals thereto in the above description.

3. Alarm Control Method

Next, an example of an alarm control instruction based on a determination result of a sleep state will be described. Specifically, a description will be given of an example in which an instruction for alarm cancellation (OFF) is performed, an example in which an instruction for alarm setting (ON) is performed, an example in which a notification mode of an alarm is controlled, and a flow of control will be finally described with reference to a flow chart.

3.1 Cancellation Instruction

As described above, when a user has already got up, it is not possible to exhibit an effect of making the user transition to an awakened state even when an alarm is brought into operation at the hour which is set in advance. In addition, there is a disadvantage of making the user have an unpleasant feeling due to unnecessary light emission or generation of a sound or forcing the user to perform an operation for stopping an alarm.

Consequently, in the present embodiment, as described above, it is assumed that an instruction for alarm cancellation is given to the alarm control unit 130 when it is determined that a user has transitioned from a sleep state to an awakened state on the basis of pulse wave information. In this manner, it is possible to suppress the operation of an alarm under an unnecessary situation, and a user is not forced to perform a stop operation.

However, a problem may occur if an alarm is immediately cancelled by the transition from a sleep state to an awakened state. For example, a case where an alarm is set to operate in the morning and a user wakes at night is considered. In this case, even when the user goes to sleep again without getting out of a bed, it is possible to determine a sleep state and an awakened state from pulse wave information with a high level of accuracy, and thus the transition from a sleep state to an awakened state is detected. In addition, when a user gets out of a bed and goes to a toilet or the like, the transition from a sleep state to an awakened state is naturally detected.

Under such a situation, it is unlikely that an awakened state of a user is continued until morning, and there is a high possibility of the user going to sleep again and transitioning to a sleep state. In this case, when the above-mentioned instruction for alarm cancellation is performed, an alarm does not operate at the hour which is set in advance, and thus there is a problem in that a user cannot wake up at the user's desired time.

Consequently, in the present embodiment, the processing unit 120 may instruct the alarm control unit 130 to perform alarm cancellation when a user transitions from a sleep state to an awakened state and it is determined that an awakened state is continued for a predetermined period of time, on the basis of pulse wave information.

Here, as the predetermined period of time, a period of time is set which is capable of discriminating between a case where an awakened state is temporary and transition to a sleep state is performed shortly after and a case where activity is continuously performed thereafter and transition to the immediate sleep state is not considered. In the above-described example, the former awakened state corresponds to an awakening in the night, and the latter awakened state corresponds to an awakening in the morning which is the hour set in advance or the hour close thereto. For example, the above-mentioned predetermined period of time should be set to be longer than at least a period of time until a user goes to a toilet from a bed and then returns. In addition, since a user cannot immediately go to sleep even though the user is lying on a bed, the predetermined period of time is required to be longer than a period of time until the user transitions from a rest state to a sleep state. As an example, the predetermined period of time may be preferably set to be a period of time equal to or longer than several tens of minutes. However, since there are differences among individual users in such a temporary period of time until transition from an awakened state to a sleep state is performed, the above-mentioned predetermined period of time may be set using information regarding history of a sleep state of a target user, and the like.

In this manner, it is possible to suppress the possibility of an alarm being cancelled under a situation where it is preferable to continue the setting (ON) of the alarm. Therefore, it is possible to suppress a user from oversleeping and the like due to inappropriate alarm cancellation.

3.2 Setting Instruction

In the recent alarm clock application such as an alarm clock or a smartphone, it is possible to flexibly set a day of the week and the hour for bringing an alarm into operation. For example, it is possible to set a designated time such that a user who is an office worker brings an alarm into operation early in the morning in accordance with attendance at work on a working day (for example, Monday to Friday) and brings an alarm into operation at a relatively late hour because of the needlessness of attendance on a day off (for example, Saturday and Sunday).

However, even when a day of the week and the hour can be specifically designated, the designated alarm can be either set (ON) or cancelled (OFF). For this reason, for example, when an alarm for which a designation of "8 o'clock on Monday morning" is made, it is necessary to appropriately switch between the setting and cancellation of the alarm when there is an attempt to realize a desire for bringing the alarm into operation on the first Monday in June, but not bringing the alarm into operation on the second Monday in June.

However, the switching between the setting and cancellation of an alarm is complicated and undesirable for a user. Further, the setting of an alarm is often performed before going to sleep. However, when a setting operation is performed before going to sleep, sympathetic nerves become dominant due to a reduction of attention to the setting, and thus there is a concern of the user's sleep being disturbed.

Consequently, in the present embodiment, when it is determined that a user has transitioned from an awakened state to a sleep state on the basis of pulse wave information, the processing unit 120 may instruct the alarm control unit 130 to set an alarm.

In this manner, it is possible to set (ON) an alarm when transition to a sleep state is performed. Usually, when transition to a sleep state is performed, there is a high possibility of an alarm to be required for causing a user to transition (for causing the user to get up) from the sleep state to an awakened state again. For this reason, when an alarm is set by transition to the sleep state, it is possible to automatically set a necessary alarm.

In addition, from another viewpoint of the above-mentioned process, when it is not possible to confirm transition to a sleep state, the setting of an alarm cannot be performed. Various cases where an alarm is not desired to operate on a predetermined day of the week and at a predetermined hour are considered. For example, a day shift is performed on Monday, but there may be a case where a night shift is performed from Sunday night to Monday morning. In a broader sense, when an awakened state is continued at the hour which is set in advance and for several hours before the time, a circadian rhythm is an unexpected situation, and thus it is considered that an alarm operation at the hour which is set in advance becomes unnecessary. In other words, transition to the sleep state is set as the condition for setting an alarm, and thus it is possible to reduce the burden of a user's operation of setting an alarm and to suppress the disturbance of user's sleep due to the operation.

Meanwhile, a case is also considered where a user sleeps as usual when the user takes a holiday on a day of the week which is usually a working day and where the user does not desire to bring an alarm clock into operation in the morning of the next day (desires to sleep well). In this case, it is difficult to appropriately control the setting even when only the transition from an awakened state to a sleep state is determined. In other words, the method of the present embodiment can allow the user's burden to be reduced, but does not promise the complete automation of setting control.

Meanwhile, in this case, when it is determined that a user has transitioned from an awakened state to a sleep state and a sleep state is continued for a predetermined period of time on the basis of pulse wave information, the processing unit 120 may instruct the alarm control unit 130 to set an alarm.

For example, even when a user takes a nap for a short period of time (for example, approximately several tens of minutes to one hour), transition from an awakened state to a sleep state is detected. However, such a sleep state due to a nap is not expected to transition to an awakened state due to an alarm when the user usually gets up. The wording "alarm when the user usually gets up" used herein refers to an alarm for getting up at a timing when a day's activity is started. In the case of a general user, the alarm refers to an alarm which operates in the morning. In other words, as a result, even when transition to a sleep state which is terminated in a short period of time is performed, it is not appropriate to set an alarm. In the case of a user who does not usually take a nap, there is also a possibility of the nap being for the purpose of changing a user's circadian rhythm to a state different from normal. If so, the setting of an alarm may not be performed.

In that regard, subject to the continuation of a sleep state for a predetermined period of time is set as a condition, when such a sleep state for a relatively short period of time, that is, a sleep state different from a continuous sleep state until the vicinity of the hour which is set in advance is detected, an alarm is not set, and thus it is possible to more appropriately control the setting of an alarm. The wording "predetermined period of time" used herein refers to a period of time shorter than a general sleep time (in the case of a normal user, a sleeping duration from night till morning, six to nine hours, and the like), and may be set to be, for example, approximately one to two hours in consideration of the above-mentioned nap. In addition, with respect to the "predetermined period of time", modification such as determination of a value using history information on a sleep state of a user can be made, similar to the embodiment regarding alarm cancellation.

In the present embodiment, whether or not to perform automatic setting of an alarm based on transition to a sleep state may be changed in accordance with whether or not automatic alarm cancellation based on the above-mentioned transition to an awakened state has been performed.

Specifically, when the processing unit 120 determines that a user has transitioned from a sleep state to an awakened state and the awakened state has been continued for a predetermined period of time on the basis of pulse wave information to thereby instruct the alarm control unit 130 to cancel an alarm, the processing unit may not give an instruction for setting an alarm even when it is determined that the user has transitioned from an awakened state to a sleep state after the alarm is cancelled, on the basis of pulse wave information.

As described above, when transition from a sleep state to an awakened state is performed and the awakened state is continued for a predetermined period of time, a user's head becomes clear to a certain extent at that time, and thus it is considered that the user has a sufficient ability to think. In other words, when the user transitions to a sleep state again after the alarm is cancelled on the basis of the determination, it can be estimated that the user intentionally wants to sleep. For example, when a user is awake before an alarm operation hour of a work day on the basis of the relation of a circadian rhythm in spite of taking a holiday on a day of the week which is usually a work day, it is considered that the user attempts to rest through sleep until a relatively late time (until the time later than at least the alarm working time of a work day) during the holiday. In this case, since the user positively attempts to get sleep after the user is once set to be in an awakened state, it is not preferable to promote transition to an awakened state by setting an alarm.

In this respect, the setting of an alarm is not performed with such a configuration, and thus it is possible to appropriately control the setting and cancellation of an alarm.

However, the method of the present embodiment is not limited thereto. Even after automatic alarm cancellation based on transition to an awakened state is performed, automatic alarm setting based on transition to a sleep state may be performed as usual.

Specifically, in a case where the processing unit 120 determines that a user has transitioned from a sleep state to an awakened state and that the awakened state has been continued for a predetermined period of time on the basis of pulse wave information to thereby instruct the alarm control unit 130 to perform alarm cancellation and where it is determined that the user has transitioned from an awakened state to a sleep state after the alarm cancellation on the basis of pulse wave information, the processing unit may give an instruction for setting an alarm.

This is because at how much time after a user's awakening the user can think clearly varies greatly depending on individuals. For this reason, the user's head does not sufficiently become clear even though an awakened state is continued for a predetermined period of time. In some cases, there is also a possibility of the user going to sleep again (second sleep) without being accompanied by a clear intention. Since a sleep state based on the unintentional second sleep should not be continued until the original alarm notification hour passes, it is preferable that an alarm is set on the basis of the detection of a sleep state, similar to a basic method of the present embodiment.

As can be seen from the above description, it is difficult to fixedly set a general-purpose method capable of being applied to all users for the setting and cancellation of an alarm. Accordingly, when predetermined determination conditions are satisfied, a configuration may be adopted in which a first user is given an instruction for first alarm control and a second user is given an instruction for the second alarm control different from the first alarm control.

For example, in the above-described example, a user, who is able to wake up early in the morning and is hardly likely to fall asleep an unintentional second time, transitioning to a sleep state can be determined to be in a situation where the user is not required to get up at the original alarm notification hour. In this case, an instruction for setting an alarm may not be given.

On the other hand, a user, who is not able to wake up early in the morning and tends to fall asleep a second time and oversleep, transitioning to a sleep state can be determined to be in a situation where the user is required to get up at the original alarm notification hour, instead of being determined to be accompanied by a clear intention. In this case, an instruction for setting an alarm may be given.

Accordingly, in the present embodiment, a user type may be determined by some methods, and an instruction given to the alarm control unit 130 may be changed on the basis of a result for each type. The user type may be input by the user himself or herself, or the processing unit 120 of the biological information processing system may perform determination using history information on the sleep of a target user. In addition, various modifications can be made.

3.3 Instruction for Notification Mode

Figure 9:
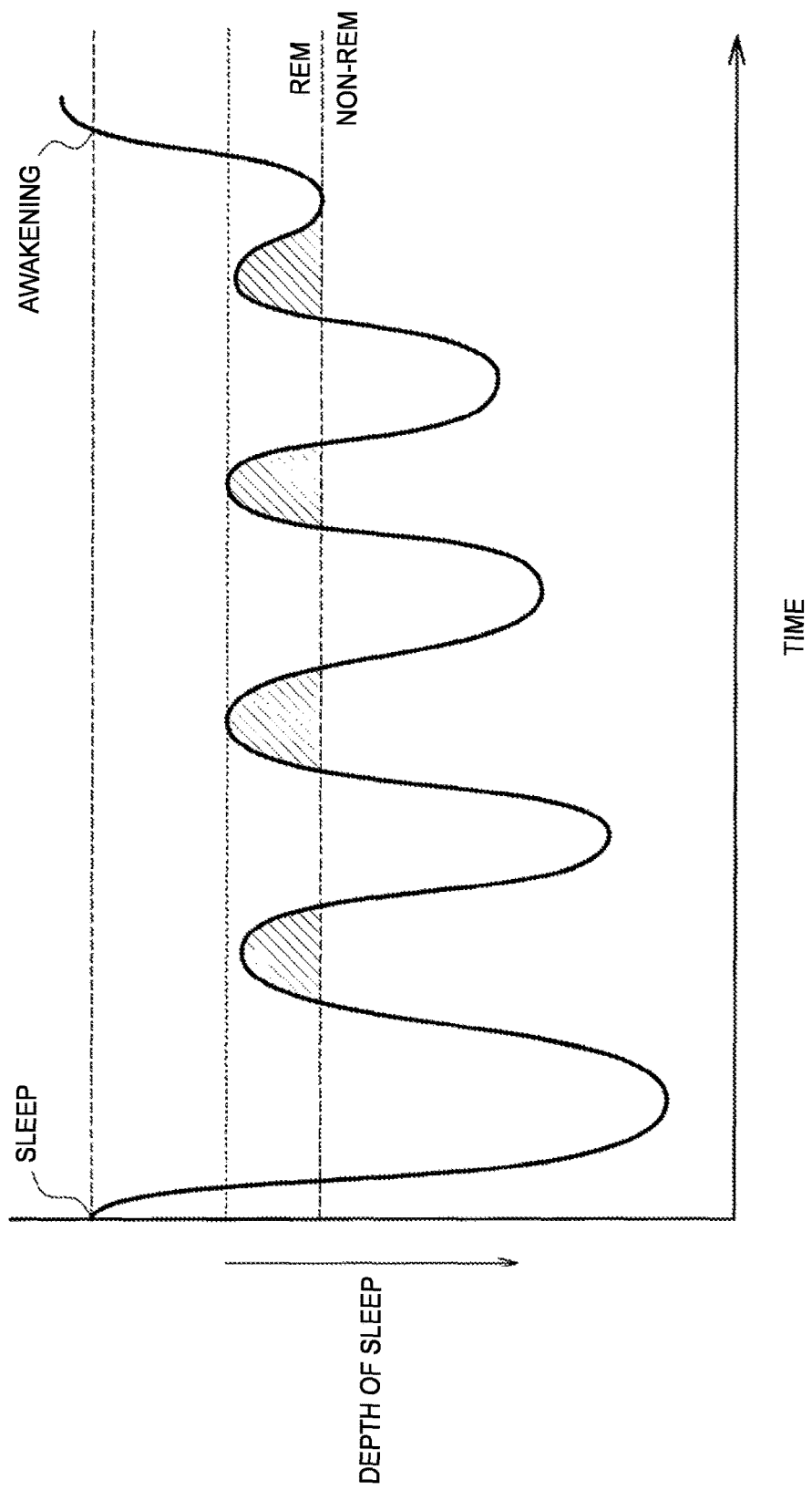
FIG. 9 is an example illustrating the depth of sleep which changes with time in a sleep state.

In recent years, study on sleep has been performed, and it has become clear how to make a human have a pleasant awakening. For example, as illustrated in FIG. 9, it has been known that the depth of sleep periodically changes with time during a period of time before a human awakes after the human goes to sleep. Specifically, a non-REM sleep state where sleep is in a relatively deep state and a REM sleep state where sleep is in a relatively light state alternately appear with a cycle time of approximately one hour and a half. A plurality of states (stage 1 to stage 4) having different depths of sleep are defined in the non-REM sleep. A deep sleep such as stage 3 or stage 4 appears in the first half of sleep. On the other hand, in the latter half of sleep (a time close to awakening), only light sleep such as stage 1 or stage 2 appears in a non-REM sleep.

In such changes in a sleep state, it is known that a pleasant awakening is possible by waking up in a relatively light sleep state. For example, there is known a method of promoting a pleasant awakening by bringing an alarm into operation in a REM sleep state. However, it has been known that one REM sleep state includes a timing suitable for an awakening and a timing unsuitable therefor, by further study. Specifically, an awakening occurring in the first half section where a user is mostly dreaming in one REM sleep state does not result in a pleasant awakening. On the other hand, an awakening occurring in the latter half section where the user finishes dreaming and occurring before and after a timing at which the REM sleep is terminated (timing when transition to the non-REM sleep is performed) results in a pleasant awakening.

As described in FIG. 6 and the like, it is possible to perform an alarm notification in various modes such as light, a sound, and vibration for the recent alarm. In addition, it is possible to make a change among individual notifications of a notification based on light, a notification based on a sound, and a notification based on vibration by controlling light intensity, sound volume, a sound type, or vibration intensity.

In view of the above-mentioned respects, a sleep state capable of identifying at least a REM sleep and a non-REM sleep is determined, and then an alarm notification is performed by selecting an appropriate mode from various modes on the basis of a determination result, and thus it is possible to realize awakening preferable to a user. Specifically, as described above, the processing unit 120 of the biological information processing system 100 may determine a sleep state of a user on the basis of pulse wave information and may preferably instruct an alarm control unit to perform an alarm notification based on a notification mode according to a sleep state.

More specifically, the processing unit 120 determines whether a sleep state of a user is a REM sleep state or a non-REM sleep state. When it is determined that the sleep state of the user is a REM sleep state, the processing unit instructs the alarm control unit 130 to perform an alarm notification based on a first notification mode. When it is determined that the sleep state of the user is a non-REM sleep state, the processing unit may preferably instruct the alarm control unit 130 to perform an alarm notification based on a second notification mode which is different from the first notification mode.

Here, a situation where the determination result is a non-REM sleep state refers to a situation where transition from a REM sleep state to a non-REM sleep state, excluding the time immediately after sleep. That is, at a timing when an alarm notification is performed, the processing unit 120 may preferably give an instruction for an alarm notification based on a second notification mode when it is determined that transition from a REM sleep state to a non-REM sleep state has been performed.

Further, as illustrated in FIG. 9, the cycles of the REM sleep state and the non-REM sleep are repeated in a sleep state. In the first and second cycles, a sleeping duration is approximately one hour and a half to three hours, and thus an awakening in such a situation is not usually assumed. For this reason, when the processing unit 120 instructs the alarm control unit 130 to perform an alarm notification when it is determined that the cycles based on the REM sleep state and the non-REM sleep state have been repeated a predetermined number of times, it is possible to perform an alarm notification at an appropriate timing.

In this manner, it is possible to change an alarm notification mode in accordance with whether a sleep state is a REM sleep state or a non-REM sleep state. Since classification of whether being a REM sleep state or a non-REM sleep state is directly linked to the pleasantness of an awakening as described above. Therefore, it is possible to perform an appropriate alarm notification by controlling a notification mode based on the classification.

When a sleep state is a REM sleep state, the execution of an alarm notification in a mode having a high awakening effect forces the sleep state to suddenly transition to an awakened state, which results in a user's unpleasant awakening. In addition, in a case where an alarm notification is immediately started when it is determined that transition to the REM sleep state has been performed, the execution of the alarm notification in a mode having a high awakening effect results in a concern of a user awaking in the first half in the REM sleep state which is not suitable for an awakening. In view of the above description, a notification mode having a relative low awakening effect may be selected in the REM sleep state.

On the other hand, the non-REM sleep assumed herein is a sleep state appearing after an alarm notification based on the first notification mode is performed, as described above. For this reason, since the non-REM sleep mentioned here is a timing which is suitable for a user's awakening, a notification based on a notification mode having a relatively high awakening effect may be performed.

For example, since it is known that reaction to a stimulus based on light is dull in a REM sleep state, it is considered that light is used as the first notification mode as described above. On the other hand, since it is also known that an auditory stimulus reacts relatively sensitively in a sleep state, the second notification mode may use a sound as described above.

However, since a mode having a low awakening effect is set in a REM sleep state and the mode may be preferably shifted to a mode having a high awakening effect, the first and second notification modes are not limited thereto. For example, an alarm notification based on a slight vibration may be performed as the first notification mode. Alternatively, a difference in an awakening effect may be given to both the first and second notification modes by changing a sound type while using a sound. In other words, the first notification mode may be an alarm notification based on a first type of sound, and the second notification mode may be an alarm notification based on a second type of sound. In a narrow sense, the first type of sound is a sound having an awakening effect lower than that of the second type of sound. Specifically, it is considered that a natural sound such as a birdcall is used as the first type of sound due to its low awakening effect and a sound such as a human voice or a bell is used as the second type of sound due to its high awakening effect. In addition, various modifications can be made to specific examples of the first and second notification modes.

Figure 10:
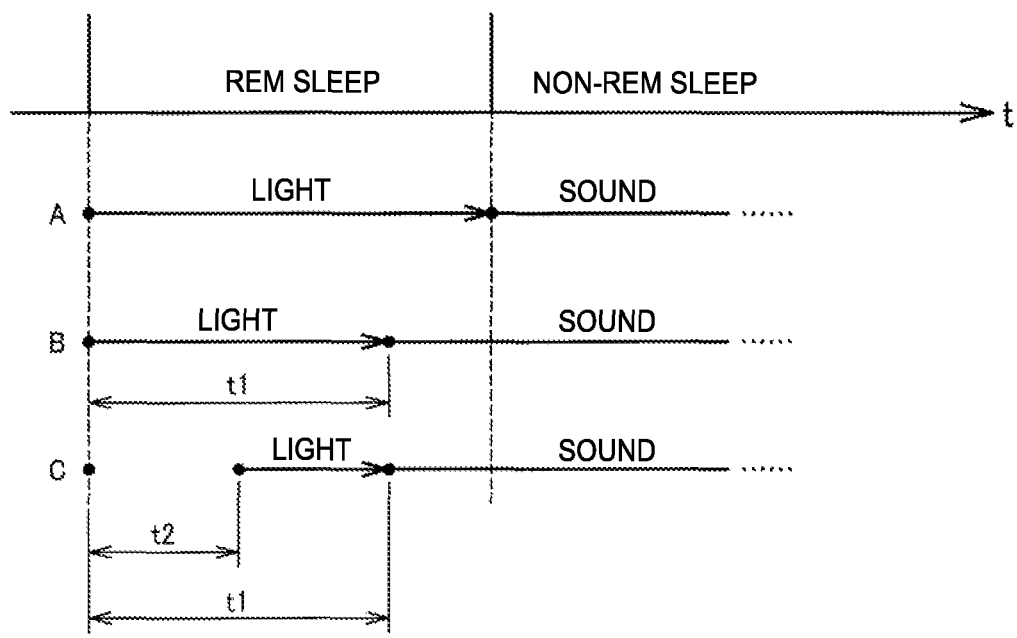
FIG. 10 is a diagram illustrating a control timing of a notification mode.

Here, the first notification mode is set when the determination result is a REM sleep state, and the second notification mode is set when the determination result is a non-REM sleep state. For this reason, an example illustrated in "A" of FIG. 10 is considered as a specific example of a notification timing. In "A" of FIG. 10, a notification based on the first notification mode (light in the example of FIG. 10) is performed from a timing when the determination result is a REM sleep state, and the notification is continued until a timing when the determination result is a non-REM sleep state. A notification based on the second notification mode (sound in the example of FIG. 10) is performed from a timing when the determination result is a non-REM sleep state. Meanwhile, in FIG. 10, although the end point of the notification based on the second notification mode is not written clearly, the notification ends, for example, at a timing when a user is awake and performs a stop operation.

However, the notification timing is not limited thereto, and various modifications can be made. For example, the processing unit 120 may instruct the alarm control unit 130 to perform an alarm notification based on the first notification mode before a first predetermined period of time t1 elapses after the determination result is a REM sleep state, and may instruct the alarm control unit 130 to perform an alarm notification based on the second notification mode which is different from the first notification mode after the first predetermined period of time t1 elapses after the determination result is a REM sleep state or when the determination result is a non-REM sleep state.

This is illustrated in "B" of FIG. 10. As described above, transition to an awakened state has no problem in the latter half of a REM sleep state which is a timing of such an extent that dreaming is finished although the first half of the REM sleep is not suitable for an awakening. In other words, when time elapses to a certain extent from the start of the REM sleep state, an alarm notification in the second notification mode having a high awakening effect may be performed without waiting for transition to a non-REM sleep state. Here, the length of the first predetermined period of time t1 may be set to a value capable of expecting that an approach is made to the latter half of a general REM sleep state (dreaming is finished to a certain extent) after the time t1 has elapsed from the start of the REM sleep. For example, when the length of the general REM sleep is set to T, the relation of t1=T×x may be established. In this case, x may be set to, for example, approximately 0.7 to 0.8. Meanwhile, there may be a possibility of transition to the non-REM sleep being performed before the time t1 elapses after the determination result is the REM sleep state depending on a sleep state of a user. In this case, since there is no reason to continue an alarm notification in a mode having a low awakening effect, an alarm notification in the second notification mode may be started at a timing when the determination result is the non-REM sleep state, similar to A of FIG. 10.

In addition, the processing unit 120 may give an instruction for an alarm notification based on the first notification mode after the determination result is the REM sleep state and then a second predetermined period of time t2 elapses.

This is illustrated in C of FIG. 10. As described above, the first half of the REM sleep is not suitable for an awakening. As long as there is the possibility of a user awaking by a stimulus of the notification in spite of an alarm notification based on the first notification mode having a low awakening effect, it may not be preferable that the alarm notification based on the first notification mode is performed immediately from a timing when the determination result is the REM sleep state. For this reason, as illustrated in C of FIG. 10, in the first section for which an awakening is not particularly suitable in the REM sleep state, an alarm notification may be started after the time t2 elapses without performing an alarm notification based on the first notification mode. Meanwhile, in C of FIG. 10, although transition to an alarm notification based on the second notification mode after the time t1 elapses is performed similar to B of FIG. 10, various modifications such as a combination with A of FIG. 10 can be made.

In addition, the processing unit 120 may instruct the alarm control unit 130 to gradually increase the notification strength of an alarm in accordance with an elapsed time from the start of an alarm notification in the alarm control unit 130. Specifically, the processing unit 120 may instruct the alarm control unit 130 to gradually increase the light intensity of light in accordance with an elapsed time from the start of an alarm notification based on light, or may give at least one of an instruction for the alarm control unit 130 to change a sound type in accordance with an elapsed time from the start of an alarm notification based on a sound and an instruction for the alarm control unit to gradually increase the sound volume of a sound.

As described above, since it is not preferable that an awakening is suddenly promoted by giving a strong stimulus from the start of an alarm notification, a notification having a high awakening effect (strong stimulus) may be gradually performed by performing transition from an alarm notification based on the first notification mode to an alarm notification based on the second notification mode. In this case, it is possible to realize a more natural awakening by gradually strengthening also in each notification mode.

3.4 Details of Process

Figure 11:
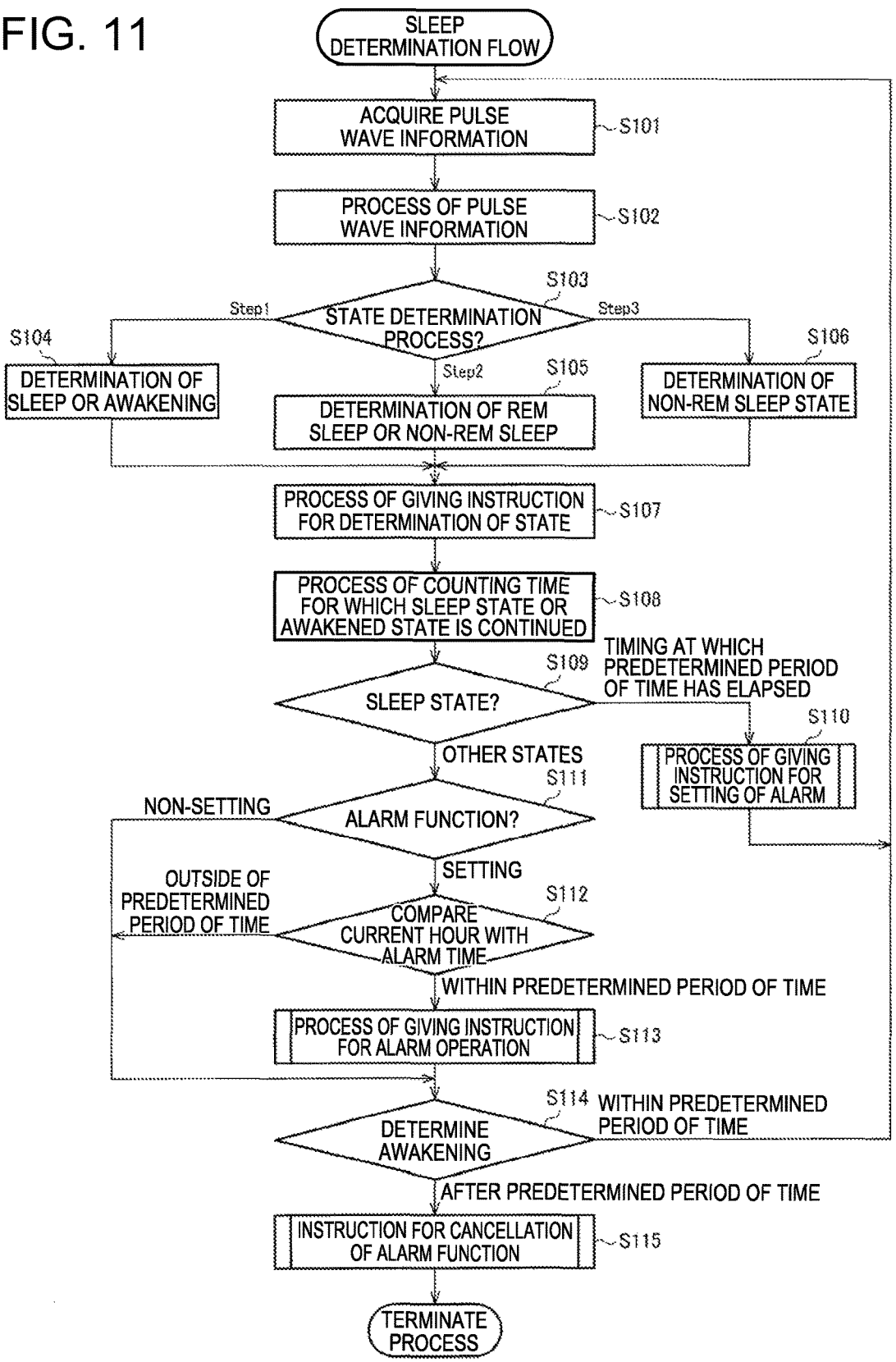
FIG. 11 is a flow chart illustrating processing according to the present embodiment.

A flow of the above-described process will be described with reference to flow charts of FIGS. 11 to 16. FIG. 11 is a flow chart illustrating the entire processing of the present embodiment. When this process is started, first, the pulse wave information acquisition unit 110 acquires pulse wave information (S101), and the processing unit 120 processes the pulse wave information (S102). The process in S102 is, for example, a process of obtaining a pulse rate, a pulse period, and the like.

Next, it is selected which determination process is performed as a process of determining a state (S103). As a specific determination, determination of whether the state is a sleep state or an awakened state (S104), determination of whether the state is a REM sleep state or a non-REM sleep state in a case of a sleep state (S105), and determination of which stage (which one of stage 1 to stage 4) the non-REM sleep state corresponds to, in a case of a non-REM sleep state (S106) are considered.

The determination of S105 is a more detailed determination process than that of S104, and the determination of S106 is a more detailed determination process than that of S105. Various modifications can be made to until which determination among the determinations is performed, depending on a situation. For example, when only the setting and cancellation (ON and OFF) are performed, the determination of S104 is sufficient. When the control of a notification mode based on a sleep state, the determination of S105 is required. Although the determination of S106 is not necessarily performed, a flexible alarm control may be realized by performing more detailed determination of a sleep state.

When determination details are decided, an instruction for the execution of the decided determination is given (S107). A specific method of determining a state will be described later. It is counted how long a sleep state or an awakened state is continuously performed, on the basis of a determination result (S108).

Next, the determination of whether being a timing at which the sleep state is continued for a predetermined period of time is performed on the basis of a counting result of S108 (S109). The wording "predetermined period of time" used herein refers to a period of time which is longer than a sleeping duration in a sleep state in a relatively short period of time such as a nap. The wording "timing at which a predetermined period of time has elapsed" used in S109 refers to a situation in which the current sleep state can be determined not to be a nap or the like but to be a continuous sleep state until the vicinity of the hour which is set in advance. Accordingly, in this case, an instruction for the setting (ON) of an alarm is given (S110).

Figure 12:
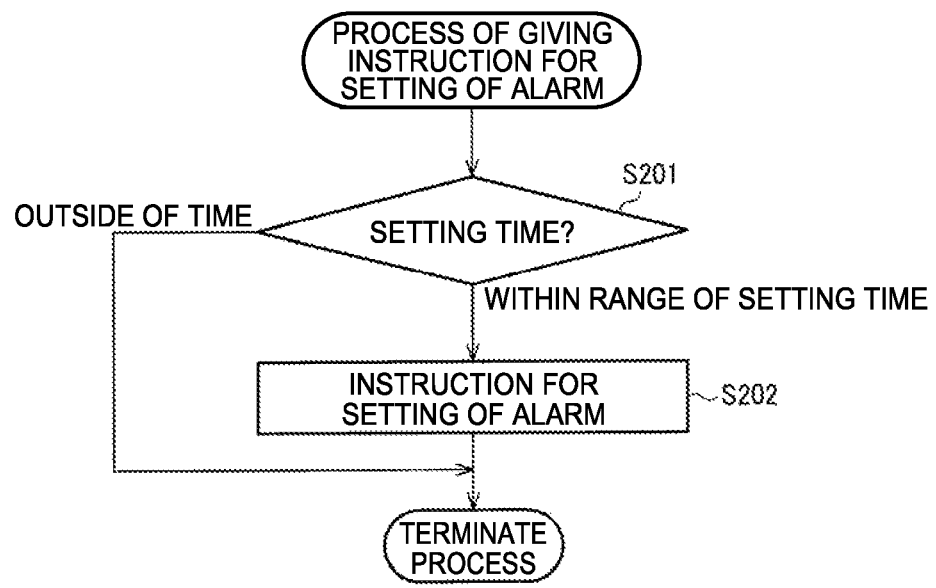
FIG. 12 is a flow chart illustrating a process of giving an instruction for setting an alarm.

A flow chart showing the process of S110 is illustrated in FIG. 12. In this process, first, the hour at which an alarm which is set in advance operates is compared with the current hour, and it is determined whether the time is within a range of a predetermined period of time (S201). For example, an alarm operating at "8 o'clock on Friday morning" is set, it cannot be said that it is appropriate to set (ON) the alarm to Monday night by transition to a sleep state. This is because the wording "situation in which it is effective to bring an alarm at 8 o'clock on Friday morning into operation" refers to a case where a continuous sleep state until a setting hour is confirmed and the wording "sleep state" refers to a sleep state which is generally started in a time zone of the night from Thursday to Friday. In other words, when an alarm is set for the reason that a sleep state is continued at night on Monday, the alarm operates even when a night shift is performed from Thursday night to Friday morning and the alarm on "8 o'clock on Friday morning" becomes unnecessary. The determination of S201 is used to suppress such a situation, and is a process of performing the determination of whether being a time zone in which an alarm associated with a predetermined day of the week and the hour may be set (ON). When it is determined in S201 that the time is within a range of a predetermined period of time, an instruction for setting an alarm is given (S202). Otherwise, the process is terminated without setting an alarm.

After the process of S110 is performed, the process returns to S101 to continue the process. In addition, in the determination of S109, in a case other than the timing at which a predetermined period of time has elapsed, the process proceeds to S111. Specifically, it is determined whether or not an alarm is set (ON) (S111). When an alarm is set, a process of comparing the current hour with the alarm hour is performed to determine whether or not the alarm time is within a range of a predetermined period of time (S112). When the determination result of S112 is YES, an instruction for the corresponding operation of the alarm is given (S113). In addition, when an alarm is not set (cancellation, OFF) in S111, the process proceeds to S114 without performing the process of S113 in a case other than the predetermined period of time in S112.

Meanwhile, in the present embodiment, as described above, an alarm notification mode is controlled depending on a sleep state (a REM sleep state or a non-REM sleep state). For this reason, the hour at which a notification is started is adjusted on the basis of a determination result of a sleep state, and the notification is not necessarily started at the hour which is set in advance. However, even though a pleasant awakening is obtained, it cannot be said that a notification performed at the hour different from a notification hour (that is, a desired getting-up hour) which is set by a user is a preferable notification. Accordingly, deviation is permitted to occur between an alarm operation hour and a notification hour which is set in advance, but it is noted that the deviation should not become excessively large. The wording "predetermined period of time" of S112 refers to a permissible amount of the deviation. Since it is not preferable that the hour of getting-up becomes drastically later than the hour which is set in advance, the above-mentioned predetermined period of time may show only deviation to the hour side which is earlier than a setting hour as a reference time (for example, the hour from the setting hour to thirty minutes before the setting hour is set to be within a predetermined period of time), and various modifications can be made.

Next, a flow of a specific process of an alarm operation instruction in S113 will be described with reference to FIG. 13. When this process is started, first, information regarding whether an alarm notification based on any notification mode has been selected is acquired (S301). It is determined whether or not an alarm notification based on illumination has been selected, on the basis of the information (S302). When the determination result is Yes, the alarm notification based on illumination is started (S303). In addition, it is determined whether or not an alarm notification based on a sound has been selected, on the basis of the information (S304). When the determination result is Yes, the alarm notification based on a sound is started (S305).

Figure 13:
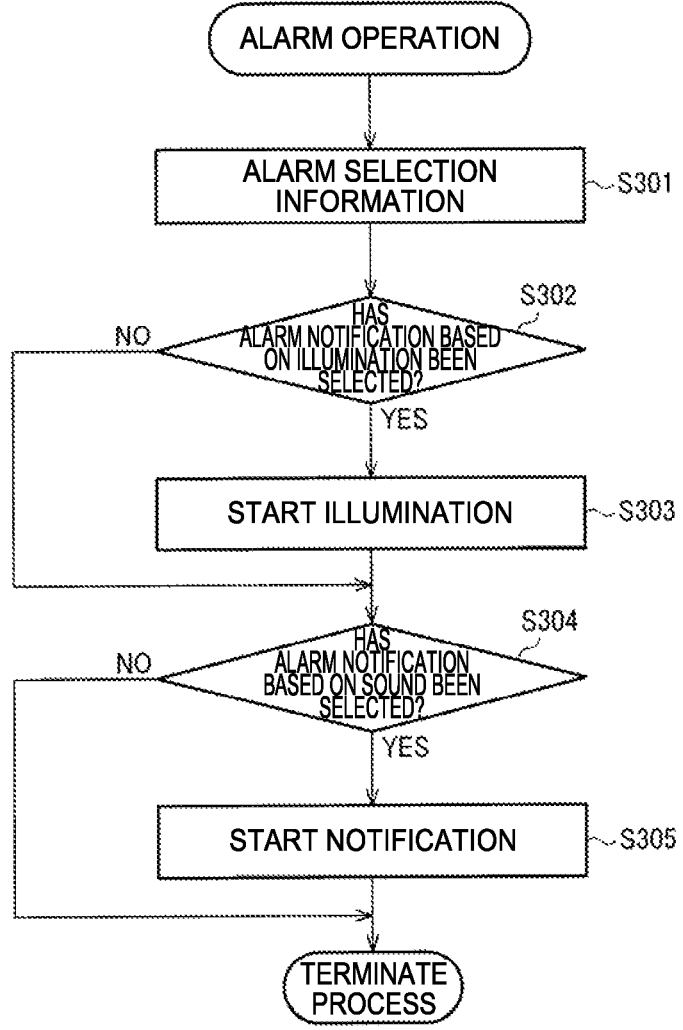
FIG. 13 is a flow chart illustrating alarm operation processing.
Figure 14:
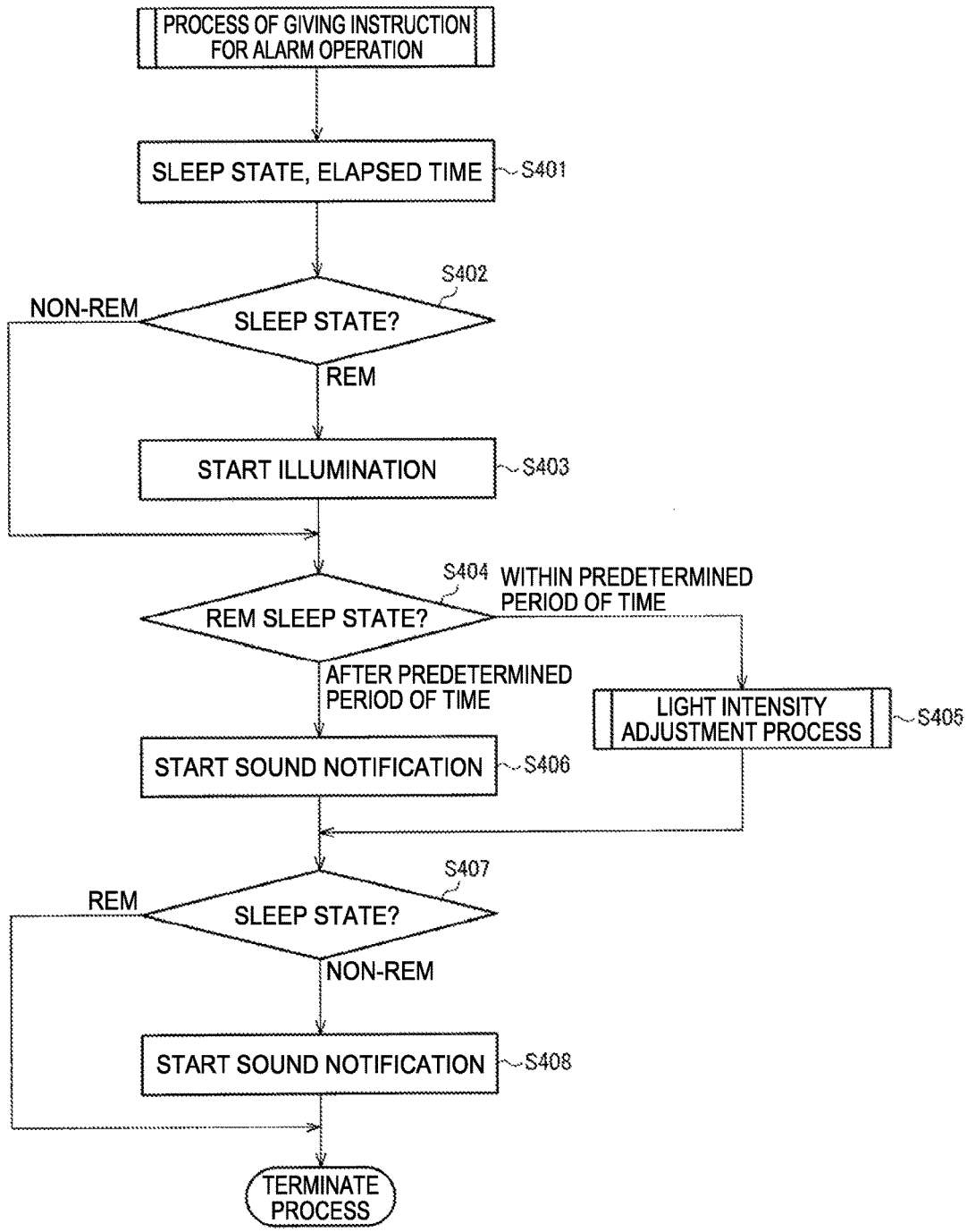
FIG. 14 is another flow chart illustrating alarm operation processing.

Meanwhile, FIG. 13 illustrates a flow of a general alarm operation. However, in the present embodiment, a notification mode may be decided depending on whether a sleep state is a REM sleep state or a non-REM sleep as described above. A flow of the process of S113 in this case is illustrated in FIG. 14. When this process is started, first, it is determined whether a sleep state is a REM sleep state or a non-REM sleep state and how long the REM sleep state has been continued from the start of the process when the sleep state is a REM sleep state (S401). Condition branching is performed according to whether the sleep state is a REM sleep state or a non-REM sleep state (S402). When the sleep state is a REM sleep state, an alarm notification based on light is started (S403). Here, the notification of S403 is an alarm notification based on the first notification mode in a broader sense.

When the determination result is in S402 is a non-REM sleep state, or after the process of S403 is performed, a time having elapsed from the start of the REM sleep state is determined (S404). When the determination result in S404 is being within a predetermined period of time, an alarm notification based on light is continued by adjusting light intensity. The wording "predetermined period of time" in S404 refers to a period of time corresponding to t1 mentioned above.

Figure 15:
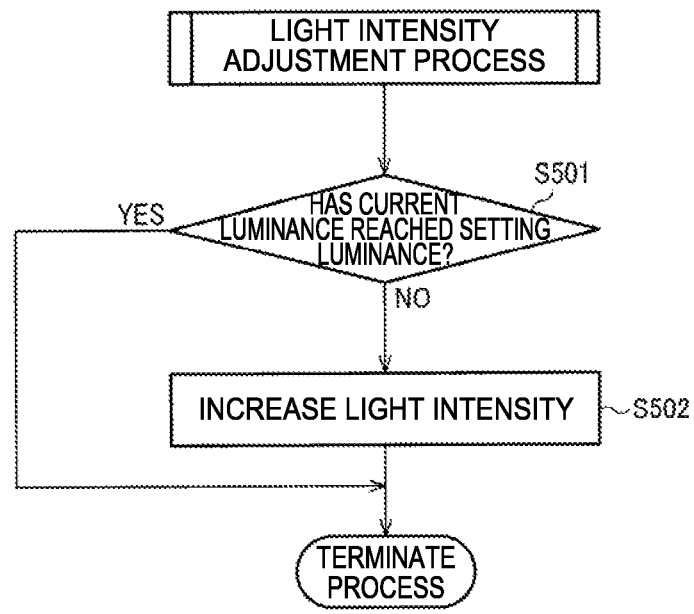
FIG. 15 is a flow chart illustrating a light intensity adjustment process.

A flow chart showing a flow of the process of S405 is illustrated in FIG. 15. In the process of adjusting light intensity, first, it is determined whether or not the current luminance reaches a setting luminance (for example, an upper limit luminance) (S501). When the determination result is No, a process of increasing light intensity is performed (S502).

On the other hand, when the predetermined period of time t1 has elapsed in S404, an alarm notification based on a sound is started (S406). Here, the notification in S406 is an alarm notification based on the second notification mode in a broader sense.

The determination of whether being a non-REM sleep state is performed (S407). When the determination result is a non-REM sleep state, an alarm notification based on a sound is started (S408). Here, the notification in S408 is an alarm notification based on the second notification mode in a broader sense, similar to that in S406.

The above description is details of the process of S113. After the process of S113 is performed, it is determined whether or not a predetermined period of time has elapsed from the start of an awakened state (S114). The wording "predetermined period of time" used herein refers to a period of time capable of discriminating between whether an awakened state is temporary and transitions to a sleep state before long and whether activity is continuously performed thereafter and transition to the immediate sleep state is not considered. According, as described above, when a predetermined period of time has elapsed, an instruction for alarm cancellation is given (S115), and the process is terminated. In a case of being less than the predetermined period of time, the process returns to S101 to continue the process.

Figure 16:
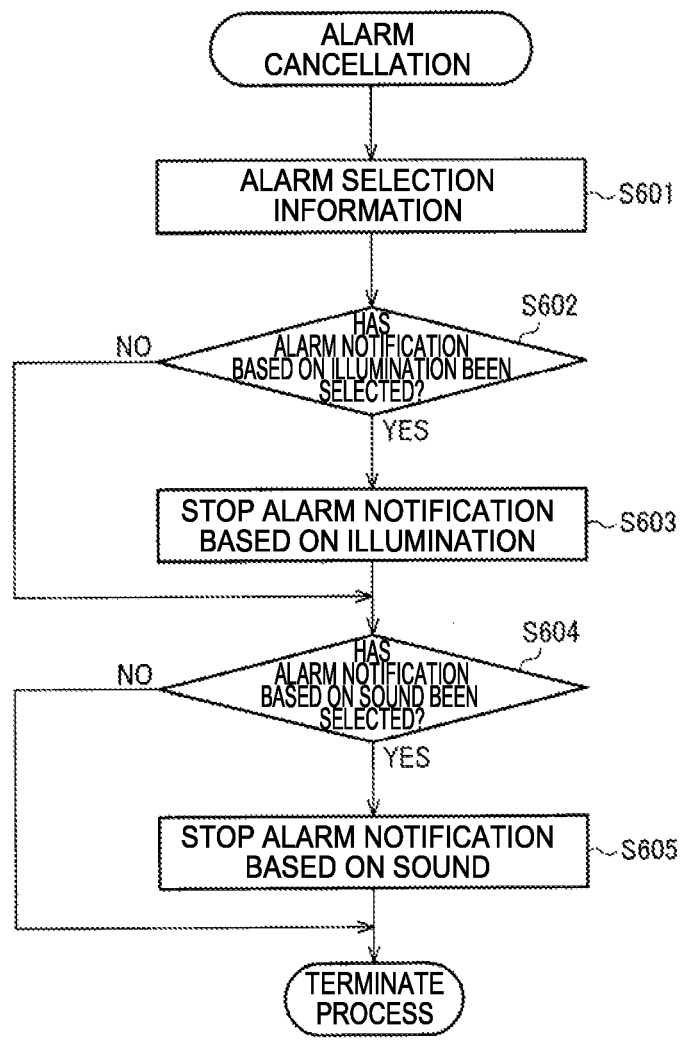
FIG. 16 is a flow chart illustrating a process of giving an instruction for alarm cancellation.

Meanwhile, a flow chart showing a flow of the process of S115 is illustrated in FIG. 16. When this process is started, first, information regarding whether an alarm notification has been selected based on any notification mode is acquired (S601). It is determined whether or not an alarm notification based on illumination has been selected, on the basis of the information (S602). When the determination result is Yes, the alarm notification based on illumination is stopped (S603). In addition, it is determined whether or not an alarm notification based on a sound has been selected, on the basis of the information (S604). When the determination result is Yes, the alarm notification based on a sound is stopped (S605).

4. Method of Determining Sleep State or Awakened State Based on Pulse Wave Information Next, a description will be given of a method of determining whether a user is in a sleep state or an awakened state on the basis of pulse wave information and a method of determining the depth (in a narrow sense, a REM sleep state or a non-REM sleep state) of the sleep in the case of a sleep state.

For example, a photoelectric sensor is used as a pulse wave sensor. In this case, a method of detecting reflected light or transmitted light of light with which a living body is irradiated, using the photoelectric sensor, is considered. Since the amount of irradiation light absorbed into the living body and the amount of irradiation light reflected from the living body vary depending on the blood flow within a blood vessel, sensor information detected by the photoelectric sensor serves as a signal corresponding to the blood flow and the like. Thus, it is possible to acquire information regarding a pulse (heartbeat, pulsation) by analyzing the signal.

Figure 17A:
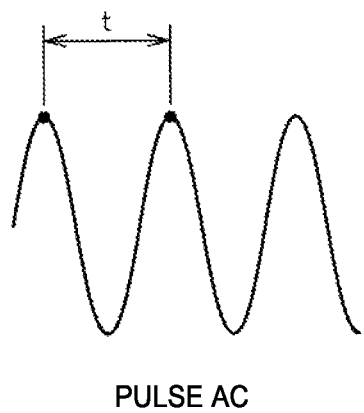
FIG. 17A is a diagram illustrating a pulse AC signal and a pulse period.

Specifically, a high blood flow and a low blood flow of a user are periodically repeated by a heart pulsation. In other words, it is possible to obtain a heart rate and a pulse period by using an AC component (pulse AC) in a pulse wave signal. For example, it is assumed that a pulse AC signal as illustrated in FIG. 17A has been acquired. In FIG. 17A, a horizontal axis represents time, and a vertical axis represents signal strength. In this case, one cycle of the pulse AC signal having periodicity corresponds to one stroke of the heart. For this reason, a pulse rate (heart rate) is obtained from the frequency of the pulse AC signal, and a pulse period which is a period of time during one stroke of the heart serves as time indicated by "t" of FIG. 17A. Meanwhile, since a usual pulse rate serves as the number of times per minute, sixty times the frequency of a pulse AC corresponds to a pulse rate which is generally used.

Here, the processing unit 120 of the present embodiment may determine an autonomic nerve activity state on the basis of pulse wave information and may perform the determination of whether being a sleep state or an awakened state on the basis of the autonomic nerve activity state.

An autonomic nerve includes a sympathetic nerve and a parasympathetic nerve, which fluctuate in an activity state during a day and each of the four seasons. In general, the sympathetic nerve is dominant at the time of activity during a day, and the parasympathetic nerve is dominant at the time of activity during the night. In the season, the sympathetic nerve is dominant toward winter from fall, and the parasympathetic nerve is dominant toward summer from spring. The reason for being frequently sleepy in spring is because a parasympathetic nerve becomes more dominant. In this manner, in order to perform transition from an awakened state to a sleep state, the activity of the parasympathetic nerve is required to change to predominance, rather than the activity of the sympathetic nerve. It is possible to determine a sleep state by observing the sleep state on the basis of the pulse period obtained from the pulse wave information.

In order to determine an autonomic nerve activity state from pulse wave information, first, time-series data of a pulse period is acquired by measuring a pulse period indicated by "t" of FIG. 17A for a certain period of time. The pulse period fluctuates (varies) without being necessarily constant all the time. The fluctuation is known to occur due to the activity of a sympathetic nerve and the activity of a parasympathetic nerve, and it is known that the fluctuation extent due to the activity of a sympathetic nerve and the fluctuation extent due to the activity of a parasympathetic nerve are different from each other.

Figure 17B:
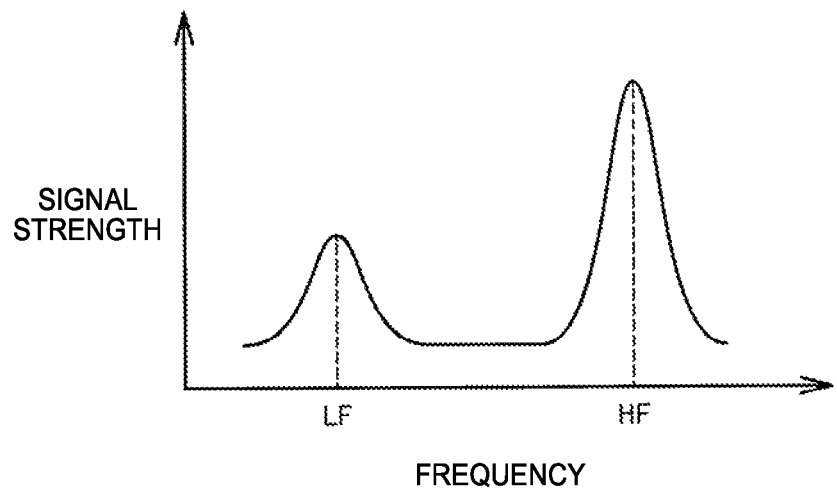
FIG. 17B is a diagram illustrating a process of obtaining LF and HF from pulse wave information.

Consequently, the time-series data of a pulse period is frequency-converted. An example of frequency-converted data is illustrated in FIG. 17B. As can be seen from FIG. 17B, a peak LF having a relatively low frequency and a peak HF having a relatively high frequency are acquired from frequency-converted data.

Here, LF indicates a slow change in a pulse period, and mainly reflects the activity of a sympathetic nerve. On the other hand, HF indicates a rapid change in a pulse period, and mainly reflects the activity of a parasympathetic nerve. Strictly speaking, LF is capable of reflecting both a sympathetic nerve and a parasympathetic nerve. However, the reflection of the activity of a sympathetic nerve will be mainly described for the purpose of simplifying the description.

In view of such characteristics, a ratio of LF to HF (for example, a ratio between signal strengths at the respective peaks) is obtained, and thus it is possible to determine which one of a sympathetic nerve and a parasympathetic nerve is dominant during a measurement period of pulse wave information.

Various methods of determining a sleep state from LF and HF are considered. For example, a value of LF/HF may be used. The LF/HF has a larger value as a sympathetic nerve becomes dominant, and has a smaller value as a parasympathetic nerve becomes dominant. Accordingly, a first threshold value Th1 is set. In the case of LF/HF>Th1, a sympathetic nerve is dominant, and thus the determination result may be an awakened state. In the case of LF/HF≤Th1, a parasympathetic nerve is dominant, and thus the determination result may be a sleep state. In addition, a second threshold value Th2 (<Th1) is set with respect to a sleep state. In the case of TH1≥LF/HF>Th2, a sympathetic nerve is relatively dominant in the sleep state, and thus it may be determined that the sleep is in a light state (REM sleep state). In the case of LF/HF≤Th2, a parasympathetic nerve is dominant, and thus it may be determined that the sleep is in a deep state (non-REM sleep state). In addition, when stages in the non-REM sleep state are determined (S106 in the flow chart of FIG. 11), the determination may be performed by further providing a threshold value in the non-REM sleep state.

In addition, a process may be performed not only by performing determination using the above-described simple value but also by using history information, such as pulse wave data so far, of a target user. For example, it is possible to estimate characteristics (for example, time required for one cycle of each of a REM sleep state and a non-REM sleep state) of periodicity in a sleep state of the target user with reference to the history. Since it can be seen that non-REM sleep appears continuously for a certain extent in one cycle and then REM sleep appears continuously for a certain extent, it is possible to estimate a high possibility of erroneous determination being performed when the determination using LF and HF is contrary to this premise. Further, since a situation or the like in which erroneous determination tends to occur can also be learned for each user, it is possible to expect an improvement in determination accuracy by using a result of the learning. Besides, various modifications can be made to the determination of a sleep state using LF and HF.

In addition, the processing unit 120 may determine an autonomic nerve activity state and a living body activity state on the basis of pulse wave information, and may determine a sleep state and an awakened state on the basis of the autonomic nerve activity state and the living body activity state.

The wording "living body activity state" used herein refers to a state of activity that may necessarily occur when a user maintains his or her alive state as a living being. Various living body activity states are considered, and it is possible to use an index value such as, for example, physical stress or mental stress. It is known that a pulse rate increases when such physical or mental stress is applied to a user. Accordingly, any pulse rate serving as a reference for a target user is obtained, and a living body activity state may be obtained from the degree of an increase in the current pulse rate with respect to the pulse rate. As the reference pulse rate, for example, a lowest pulse rate capable of being taken by the target user may be used. For example, a lowest pulse rate which is a minimum value of the pulse rate within a predetermined period of time may be used. Alternatively, the above-mentioned LF and HF may be used. It is known that LF increases and HF decreases when a physical or mental load is applied to a user. Accordingly, a living body activity state may be obtained from the degree of changes in LF and HF.

In addition, the biological information processing system 100 according to the present embodiment may further include the body motion information acquisition unit 140 that acquires body motion information of a user as illustrated in FIG. 7. The processing unit 120 may determine a sleep state and an awakened state on the basis of pulse wave information and body motion information.

Usually, when there is user motion (body motion), it is difficult to obtain highly accurate information from pulse wave information. For example, when pulse wave information is acquired by measuring the blood flow of a wrist portion using the apparatus illustrated in FIG. 5 or the like, a user's arm waving operation fluctuates the blood flow due to centrifugal force and the like regardless of the heartbeat, a change in the raising of the arm in the direction of a ceiling or the lowering of the arm in the direction of a floor fluctuates the blood flow due to a water head pressure regardless of the heartbeat. In addition, since the clenching or unclenching of a hand fluctuates the degree of pressing of a blood vessel, the blood flow also fluctuates. In this case, since the fluctuation of the blood flow which is not related to the heartbeat is also detected as the pulse wave information, it is difficult to accurately detect a fluctuation in the blood flow caused by the heartbeat which is originally desired to be detected.

Consequently, body motion information may be acquired by the body motion information acquisition unit 140 of the biological information processing system 100, and components (body motion noise) fluctuating the blood flow which are caused by factors other than the heartbeat which is included in the pulse wave information may be reduced using the body motion information.

In this manner, when the body motion information acquisition unit 140 is included in order to improve the accuracy of the pulse wave information, a sleep state and an awakened state may be determined from the body motion information. As an example, similarly to the method of the related art, a sleep state and an awakened state may be determined using body motion information and, independently therefrom, a sleep state and an awakened state are determined using the above-mentioned pulse wave information. It is considered that a final determination is performed using two results of both the determinations.

Alternatively, a configuration may also be adopted in which the determination of a sleep state is simply performed in advance using body motion information and is then performed using pulse wave information when a determination result of the simple determination is a sleep state. In this case, the body motion information is used in the preprocessing of the determination using the pulse wave information.

While the present embodiment has been described above, one of ordinary skill in the art can easily understand that various modifications can be made without substantially departing from the new matters and advantageous effects of the invention. Therefore, all such modifications are included in the scope of the invention. For example, in the specification and drawings, a term described along with a different term with a broader meaning or the same meaning at least once can be replaced with the different term in any part of the specification and drawings. In addition, the configuration and operation of the biological information processing system are not limited to those described in the present embodiment, and various modifications can be made.

What is claimed is:

1. A biological information processing system comprising:
 a pulse wave information acquisition unit that acquires pulse wave information of a user; and
 a processing unit that instructs an alarm control unit to:
  set an alarm to an on state when it is determined that the user has transitioned from an awakened state to a sleep state, on the basis of pulse wave information, and after the alarm is set to the on state, to perform alarm cancellation to place the set alarm to an off state when it is determined that the user has transitioned from a sleep state to an awakened state, on the basis of the pulse wave information, and the awakened state has been continued for a predetermined period of time, wherein the predetermined period of time is at least twenty minutes.

2. The biological information processing system according to claim 1, wherein the processing unit instructs the alarm control unit to set the alarm to the on state when it is determined that the user has transitioned from the awakened state to the sleep state and that the sleep state has been continued for a predetermined period of time, on the basis of the pulse wave information.

3. The biological information processing system according to claim 1, wherein after the alarm cancellation is performed the processing unit does not give an instruction for setting of an alarm to an on state if it is determined that the user has transitioned from the awakened state to the sleep state.

4. The biological information processing system according to claim 1, wherein if it is determined that the user has transitioned from the awakened state to the sleep state after the alarm cancellation is performed, the processing unit gives an instruction for setting the alarm to the on state.

5. The biological information processing system according to claim 1, wherein the processing unit determines an autonomic nerve activity state on the basis of the pulse wave information, and determines the sleep state and the awakened state on the basis of the autonomic nerve activity state.

6. The biological information processing system according to claim 1, wherein the processing unit determines an autonomic nerve activity state and a biological activity state on the basis of the pulse wave information, and determines the sleep state and the awakened state on the basis of the autonomic nerve activity state and the biological activity state.

7. The biological information processing system according to claim 1, further comprising a body motion information acquisition unit that acquires body motion information of the user,
wherein the processing unit determines the sleep state and the awakened state on the basis of the pulse wave information and the body motion information.

8. The biological information processing system according to claim 1, further comprising the alarm control unit.

9. The biological information processing system according to claim 1, wherein setting the predetermined period of time is based on history of sleep of the user.

10. A biological information processing system comprising:
a processing unit that acquires pulse wave information of a user and performs setting of an alarm to an on state when it is determined that the user has transitioned from an awakened state to a sleep state on the basis of the pulse wave information, and after the alarm is set to the on state, performs alarm cancellation to place the set alarm to an off state when it is determined that the user has transitioned from a sleep state to an awakened state on the basis of the pulse wave information, and that the awakened state has been continued for a predetermined period of time, on the basis of the pulse wave information, wherein the predetermined period of time is at least twenty minutes.

11. The biological information processing system according to claim 10, wherein when it is determined that the user has transitioned from the awakened state to the sleep state and that the sleep state has been continued for a predetermined period of time, on the basis of the pulse wave information, the alarm is set to the on state.

12. The biological information processing system according to claim 10, wherein an alarm is not set to an on state if it is determined that the user has transitioned from the awakened state to the sleep state after the alarm cancellation is performed.

13. The biological information processing system according to claim 10, wherein if it is determined that the user has transitioned from the awakened state to the sleep state after the alarm cancellation is performed, the alarm is set to the on state.

14. The biological information processing system according to claim 10, wherein an autonomic nerve activity state is determined on the basis of the pulse wave information, and the sleep state and the awakened state are determined on the basis of the autonomic nerve activity state.

15. The biological information processing system according to claim 10, wherein an autonomic nerve activity state and a biological activity state are determined on the basis of the pulse wave information, and the sleep state and the awakened state are determined on the basis of the autonomic nerve activity state and the biological activity state.

16. The biological information processing system according to claim 10, wherein body motion information of the user is acquired, and the sleep state and the awakened state are determined on the basis of the pulse wave information and the body motion information.

17. The biological information processing system according to claim 10, wherein setting the predetermined period of time is based on history of sleep of the user.

18. A method of controlling a biological information processing system, the method comprising:
performing a process of acquiring pulse wave information of a user;
performing setting of an alarm to an on state when it is determined that the user has transitioned from an awakened state to a sleep state on the basis of the pulse wave information; and
performing alarm cancellation to place the set alarm to an off state when it is determined that the user has transitioned from a sleep state to an awakened state, on the basis of the pulse wave information, and the awakened state has been continued for a predetermined period of time, wherein the predetermined period of time is at least twenty minutes.

19. The method of controlling a biological information processing system according to claim 18, wherein setting the predetermined period of time is based on history of sleep of the user.

* * * * *